(12) United States Patent
Sheffield et al.

(10) Patent No.: US 12,133,638 B2
(45) Date of Patent: Nov. 5, 2024

(54) INTEGRATED CLEANING DEVICE AND SYSTEM FOR OPTICAL INSTRUMENTS

(71) Applicant: BRIGHAM YOUNG UNIVERSITY, Provo, UT (US)

(72) Inventors: Jacob L. Sheffield, Provo, UT (US); Amanda Lytle, Provo, UT (US); Jacob G. Hunter, West Lafayette, IN (US); Lance Hyatt, State College, PA (US); Larry L. Howell, Orem, UT (US)

(73) Assignee: BRIGHAM YOUNG UNIVERSITY, Provo, UT (US)

( * ) Notice: Subject to any disclaimer, the term of this patent is extended or adjusted under 35 U.S.C. 154(b) by 0 days.

(21) Appl. No.: 18/000,804

(22) PCT Filed: Jun. 1, 2021

(86) PCT No.: PCT/US2021/035287
§ 371 (c)(1),
(2) Date: Dec. 5, 2022

(87) PCT Pub. No.: WO2021/247605
PCT Pub. Date: Dec. 9, 2021

(65) Prior Publication Data
US 2023/0240522 A1    Aug. 3, 2023

Related U.S. Application Data

(60) Provisional application No. 63/034,294, filed on Jun. 3, 2020, provisional application No. 63/165,528, filed on Mar. 24, 2021.

(51) Int. Cl.
*A61B 1/12* (2006.01)
*A61B 90/70* (2016.01)

(52) U.S. Cl.
CPC .............. *A61B 1/126* (2013.01); *A61B 90/70* (2016.02); *A61B 2090/701* (2016.02)

(58) Field of Classification Search
None
See application file for complete search history.

(56) References Cited

U.S. PATENT DOCUMENTS

2009/0229067 A1    9/2009  Becker et al.
2012/0101337 A1    4/2012  Clark et al.
(Continued)

FOREIGN PATENT DOCUMENTS

JP    2008279202 A    11/2008

OTHER PUBLICATIONS

International Search Report and Written Opinion from International Application No. PCT/US2021/035287 mailed Oct. 21, 2021, 17 pages.

(Continued)

*Primary Examiner* — Eric W Golightly
(74) *Attorney, Agent, or Firm* — Dorsey & Whitney LLP

(57) ABSTRACT

A device and methodology for cleaning optical instruments. The device includes a sheath, a wiper mechanism, and an actuator. The sheath attaches to an optical instrument such that the wiper mechanism is in proximity to a lens of the optical instrument. The wiper mechanism includes a blade and a compliant deployment system having first and second curved cross members attached to the blade and sheath such that they bias the blade in a first state where the blade is in a deployed position but can de-form allowing the blade to transition to a second state in a stored position. The actuator maintains tension on the blade to keep the blade in the second state and when the actuator releases tension on blade spring energy stored by the deformation of the curved cross (Continued)

members is released transitioning the blade to the first deployed position providing a wipe of the wiper mechanism.

18 Claims, 27 Drawing Sheets

(56) References Cited

U.S. PATENT DOCUMENTS

2017/0332893 A1 11/2017 Irion et al.
2017/0354540 A1* 12/2017 Yang ...................... A61F 9/029

OTHER PUBLICATIONS

U.S. Appl. No. 63/034,294, filed Jun. 3, 2020, 30 pages.
U.S. Appl. No. 63/165,528, filed Mar. 24, 2021, 63 pages.

* cited by examiner

INTEGRATED CLEANING DEVICE AND SYSTEM FOR OPTICAL INSTRUMENTS

CROSS-REFERENCE TO RELATED APPLICATION(S)

This application is a U.S. Nationalization of PCT International Application No. PCT/US2021/035287 filed on Jun. 1, 2021, which claims priority to, and the benefit of, U.S. Provisional Application No. 63/034,294 filed Jun. 3, 2020 and U.S. Provisional Application No. 63/165,528 filed Mar. 24, 2021, the entire disclosure of each of which is incorporated herein, in its entirety, by this reference.

STATEMENT REGARDING FEDERALLY SPONSORED RESEARCH OR DEVELOPMENT

This invention was made with government support under NSF Award Nos. 1663345 and 1926024 awarded by the National Science Foundation. The government has certain rights in the invention.

FIELD OF THE INVENTION

The present invention relates to tools, and more specifically optical instruments, and in particular to in-vivo medical instruments, such as endoscopic instruments, and mechanisms for cleaning the field of view of such instruments.

BACKGROUND

Generally, many optical instruments are deployed in a manner that makes it difficult to clean the optical instruments when they are deployed and in use. For example, with the use of endoscopic tools, such as a laparoscope, it is not uncommon for the lens of the laparoscope to become obscured from fog, bodily fluids, or debris, requiring the laparoscope to be removed from the patient to be cleaned. This can happen several times during a surgical procedure.

In addition, for endoscopic tools, such tools are specifically sized to fit within a trocar for insertion into a body. As such, any cleaning device attached to such a device cannot change the shape or add significantly to the diameter of the endoscopic tool or it will no longer fit within the trocar and could impinge on body tissues undesirably during use. In addition, it is undesirable to block or otherwise obstruct the field of view of the lens of the optical instrument with a cleaning device.

Previous attempts at providing an interoperative and in vivo cleaning device, particularly for endoscopic tools such as laparoscopes, have been too bulky, obstruct the field of view, have been too complex, too expensive, or only address limited sources of visual obstructions such fogging, but lack the ability to remove physical adhesion such as fat particles.

SUMMARY

There is a need for a mechanism that can clean the lens of an endoscopic tool, such as laparoscope, without disrupting the workflow of the surgical procedure, without requiring the removal of the scope or navigating away from the surgical site, without extending outside of the diametrical or cylindrical cross-section of the delivery sheath through which it travels, and in a manner of construction that is cost-effective and in some cases disposable. The present invention is directed toward further solutions to address this need, in addition to having other desirable characteristics. In particular, unlike other proposed cleaning mechanisms, this design is minimalistic and conforms to a cylindrical cross-section of a delivery trocar at all times. In addition, when in a closed or stored state the cleaning device does not block or otherwise obstruct the field of vision of the optical instrument. In addition, the present device is less complex than prior art, and more versatile and intuitive to use than previous solutions and can be made disposable.

In accordance with example embodiments of the present invention, a device and methodology are provided for cleaning optical instruments. The device includes a sheath, a wiper mechanism, and an actuator. The sheath attaches to the optical instrument such that the wiper mechanism is in proximity to the lens of the optical instrument. The wiper mechanism includes a blade and a compliant deployment system having first and second curved cross members attached to the blade such that they bias the blade in a first state where the blade is in a deployed position but can deform allowing the blade to transition to a second state in a stored position. The actuator maintains tension on the blade to keep the blade in a second state and when the actuator releases tension on the blade spring energy stored by the deformation of the first and second curved cross members is released transitioning the blade to the first deployed position providing a wipe of the wiper mechanism.

In further accordance with embodiments and aspects of the present invention, the entire claim set submitted herewith from the claim section is incorporated herein by reference, such that all embodiments, aspects, and operable combinations thereof, are fully supported by the present specification.

BRIEF DESCRIPTION OF THE FIGURES

These and other characteristics of the present invention will be more fully understood by reference to the following detailed description in conjunction with the attached drawings, in which.

DETAILED DESCRIPTION

Figure 1:
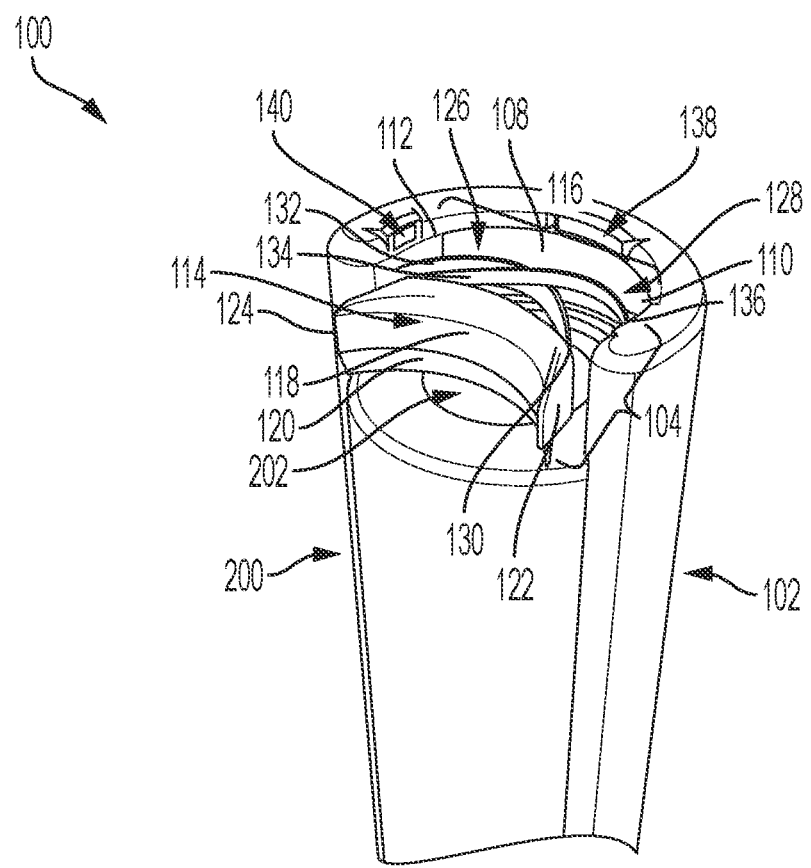
FIG. 1 depicts the distal end of a laparoscope having a wiper mechanism in accordance with one embodiment of the present invention.

An illustrative embodiment of the present invention relates to a fully compliant, lens cleaning mechanism that resides in close proximity to the lens or optics of an optical instrument. For example, the lens cleaning mechanism can be provided at the distal end of a sheath which attaches to the outside shaft of an existing elongated lens or other optical instrument (e.g. laparoscope). In other embodiments the lens cleaning mechanism can be incorporated into the optical instrument itself. The wiper mechanism is largely concealed within the walls of the sheath and has the ability to extend across the entire surface of the lens when actuated, then conforms back to the cylindrical wall. The mechanism never extends past the outer diameter of the cylindrical walls (i.e., stays within the cylindrical cross-section of the sheath and trocar at all times).

The mechanism can use internal spring energy stored in initially curved compliant beams or members which can enable it to deploy. The wiper can be deployed by releasing tension on a cable from an ex vivo trigger or other actuator on the proximal end of the scope. The same cable can then return the wiper back to the closed position. In an alternative embodiment, the relative position of which position the energy is stored or released can be reversed.

The in-vivo cleaning device and system of endoscopic instruments provides the following advantages.

Fully compliant components
  Using compliant members in the design reduces the overall number of parts required to perform its function.
  It also makes the overall design simple and un-invasive.
  This reduces manufacturing and assembly costs.
  Ease of assembly due to reduced components and lack of pin joints at this scale.
  Limits the number of parts that could potentially break off inside patient's body.

Developable mechanisms
  The mechanism resides within the walls of the sheath, which attaches to a laparoscope. This ensures that the wiper mechanism never obstructs vision during an operation except for when it is moving across the surface to perform a cleaning.
  By having the mechanism conform to the cylindrical walls, this allows the surgical staff to unimpededly insert and remove the scope through a cylindrical port (e.g. trocar).

Integration with existing laparoscopes
  Since laparoscopic optical systems are expensive and complex, the present invention easily attaches to existing laparoscopes and only requires a minimal addition of equipment.

Inexpensive
  Due to the simplicity of the design, the present invention can be manufactured to be disposable which would eliminate the need to go through the expensive re-sanitation process.

Mechanical and electronic actuation
  Although the invention can use electronic actuation to automatically set the wiping frequency, the system can also perform its function purely mechanically without any need for additional hookups.

FIGS. 1 through 27, wherein like parts are designated by like reference numerals throughout, illustrate an example embodiment or embodiments of an in-vivo cleaning device and system of endoscopic instruments, according to the present invention. Although the present invention will be described with reference to the example embodiment or embodiments illustrated in the figures, it should be understood that many alternative forms can embody the present invention. One of skill in the art will additionally appreciate different ways to alter the parameters of the embodiment(s) disclosed, such as the size, shape, or type of elements or materials, in a manner still in keeping with the spirit and scope of the present invention.

As utilized herein, the term "developable" has a specific meaning. A developable surface is a shape that can be made from a thin sheet of material without breaking or stretching. The term "developable mechanism" or "developable actuator" are interchangeable terms as utilized herein and describe a mechanism that conforms to or is created from a developable surface. Developable mechanisms can conform to or emerge from developable surfaces such as aircraft fuselages and wings, submarine hulls, rocket cones, and cylindrical minimally invasive surgery tools.

Also as utilized herein, the inventive mechanism contained within the cylindrical sleeve or sheath is considered "closed" when in an un-deployed state, nested inside the sleeve or sheath wall, and the inventive mechanism is considered "open" when in a deployed state, expanding outward and beyond the sleeve or sheath wall. In certain embodiments, the mechanism is manufactured in the "open" or deployed state.

FIG. 1 shows the integrated cleaning device 100 of the present invention. The device 100 comprises a sheath 102, a wiper mechanism 104, and an actuator 106 (not shown). The sheath 102 is sized, shaped, and configured to attach to an optical instrument 200, here a laparoscope, and having a cavity 108 positioned in proximity to a lens 202 of the optical instrument 200. The cavity 108 has a first end 110 and second end 112.

The wiper mechanism 104 is disposed within the cavity 108 of the sheath 102. The wiper mechanism 104 comprises a blade 114 and a compliant deployment mechanism 116.

The blade 114 comprises a body 118 and a lens engagement surface 120. The body 118 having first end 122 and a second end 124 opposite the first end 122. The body 118 is shaped in conformance with the size, shape, and configuration of the sheath 102. The lens engagement surface 120 extends from the body 118 and configured to wipe the lens 202 of the optical instrument 200 with movement of the blade body 118.

The compliant deployment mechanism 116 comprises a first curved cross member 126 and a second curved cross member 128. The first curved cross member 126 is on a first plane and has a first end 130 coupled to the first end 122 of the blade 114 and a second end 132 coupled to the second end 112 of the cavity 108. The second curved cross member 128 is on a second plane and a first end 134 coupled to the second end 124 of the blade 114 and a second end 136 coupled to the first end 110 of the cavity 108. The first curved cross member 126 and the second curved cross member 128 cross each other and bias the blade 114 in a first state where the blade 114 is in a deployed position but can deform allowing the blade 114 to transition to a second state in a stored position where the blade 114 is contained within the cavity 108 of the sheath 102.

The actuator 106 is configured to transition the wiper mechanism 104 between the first state to the second state wherein the actuator 106 maintains tension on the blade 114 to keep the blade 114 in a second state and when the actuator 106 releases tension on the blade 114 spring energy stored by the deformation of the first and second curved cross members 126, 128 is released transitioning the blade 114 to the first deployed position providing a wipe of the wiper mechanism 104. In certain embodiments, the actuator 106 is a cable attached to the body 118 of the blade 114 and extending through the sheath 102 to a tensioner mechanism (not shown) located distal from the wiper mechanism 104.

In certain embodiments, the integrated cleaning device 100 further comprises a port 138 in proximity to the lens 202 of the optical instrument 200 for providing a flow of gas across the lens 202. In still other embodiments, the integrated cleaning device 100 further comprises one or more sprayers 140 in proximity to the lens 202 of the optical instrument 200 for applying a fluid to the lens 202.

The components of FIG. 1 are described in more detail hereafter.

Figure 2:
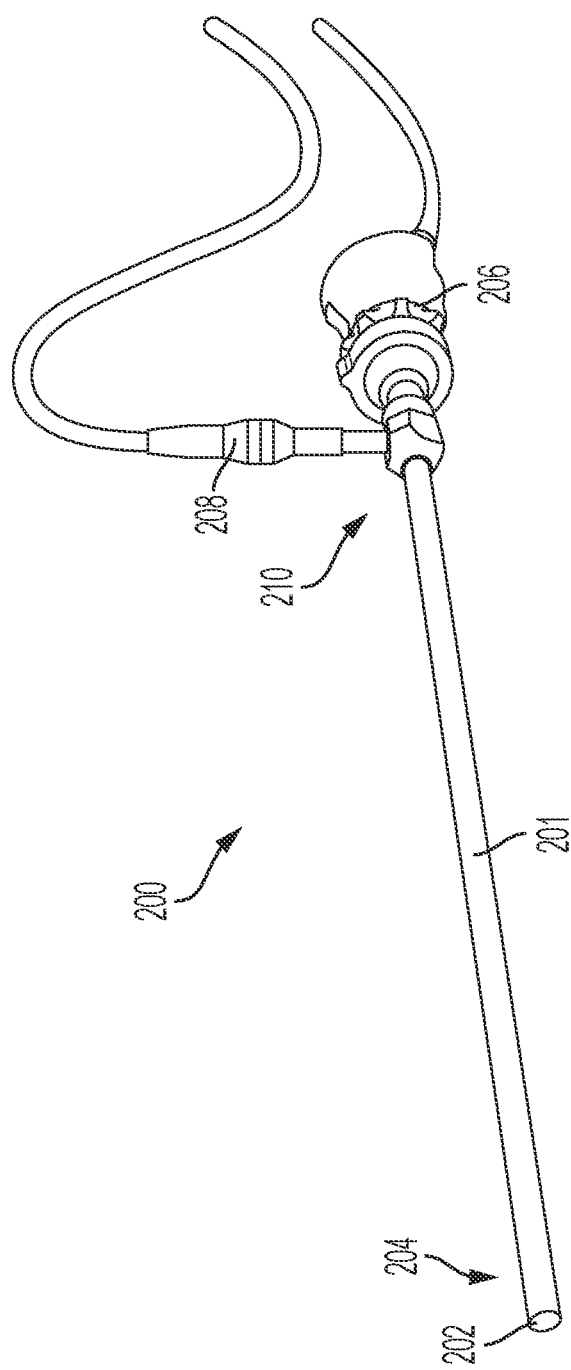
FIG. 2 depicts a zero-degree laparoscope.

FIG. 2 shows an example zero-degree laparoscope optical instrument 200 on which the integrated cleaning device 100 of the present invention can be deployed. The lens 202 is disposed at a distal end 204 of the shaft 201 of the instrument 200 which is inserted into a body and the controls 206 and optical connections 208 are located at the proximal end 210 of the shaft 201 which is in the user's control.

Wiper Mechanism

At the core of the cleaning device 100 in accordance with the present invention is the mechanical wiper mechanism 104. The wiper mechanism can also work in conjunction with other cleaning methods to be performed through attachments, specifically gas ports 138 or fluid sprayers to "spray" off the lens or apply an anti-fog coating.

The wiper mechanism 104 is actuated ex vivo (outside the body) using the actuator 106 via a mechanical or electronical tensioning means. When it is activated mechanically, a tensioner mechanism such as trigger 152 (or other wheel actuator 154) is pulled and released in order to deploy the blade 114 across the lens 202 and to return it to its undeployed state. When it is actuated electronically, the user, such as a surgeon or surgical technicians, can set the wiper mechanism 104 to wipe at a specific frequency, or specific time intervals. As well, artificial intelligence can be used for the wiper mechanism 104 to wipe when a certain level of obscurity is recognized.

Figure 3:
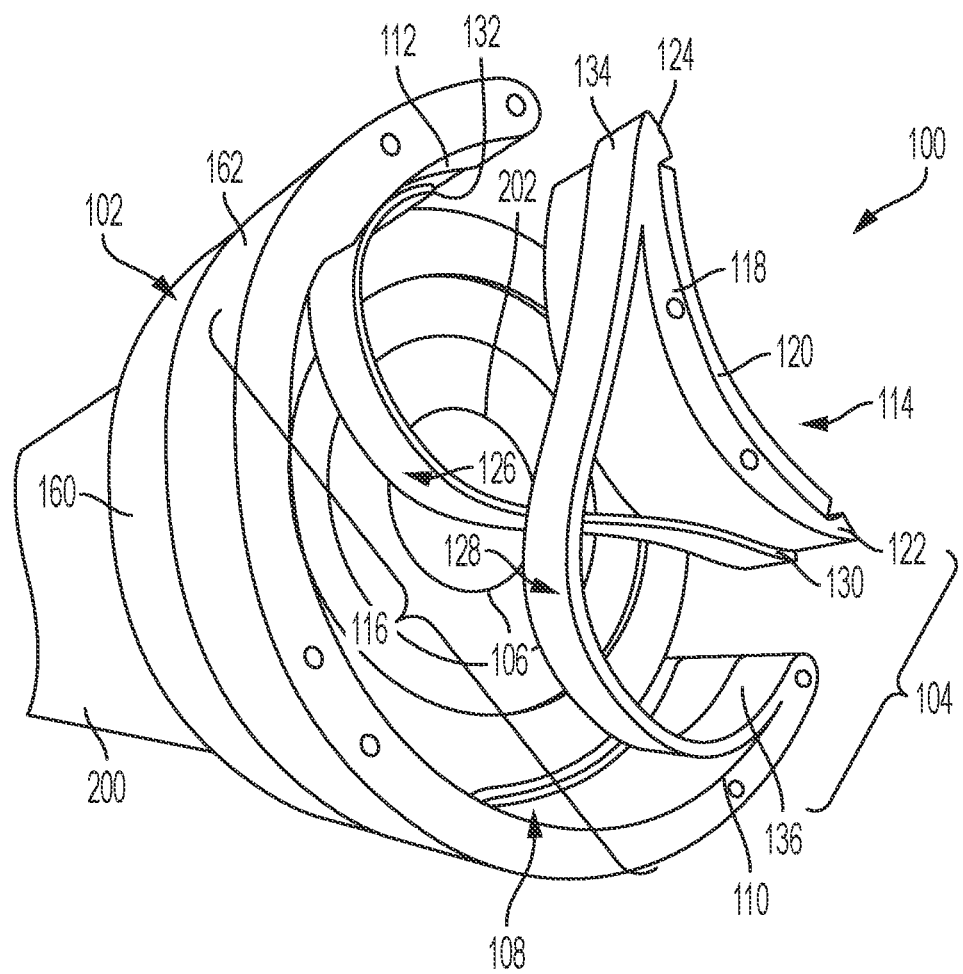
FIG. 3 depicts an example base mechanism with two initially curved members that are derived from elongated cross axis flexural pivots.
Figure 4:
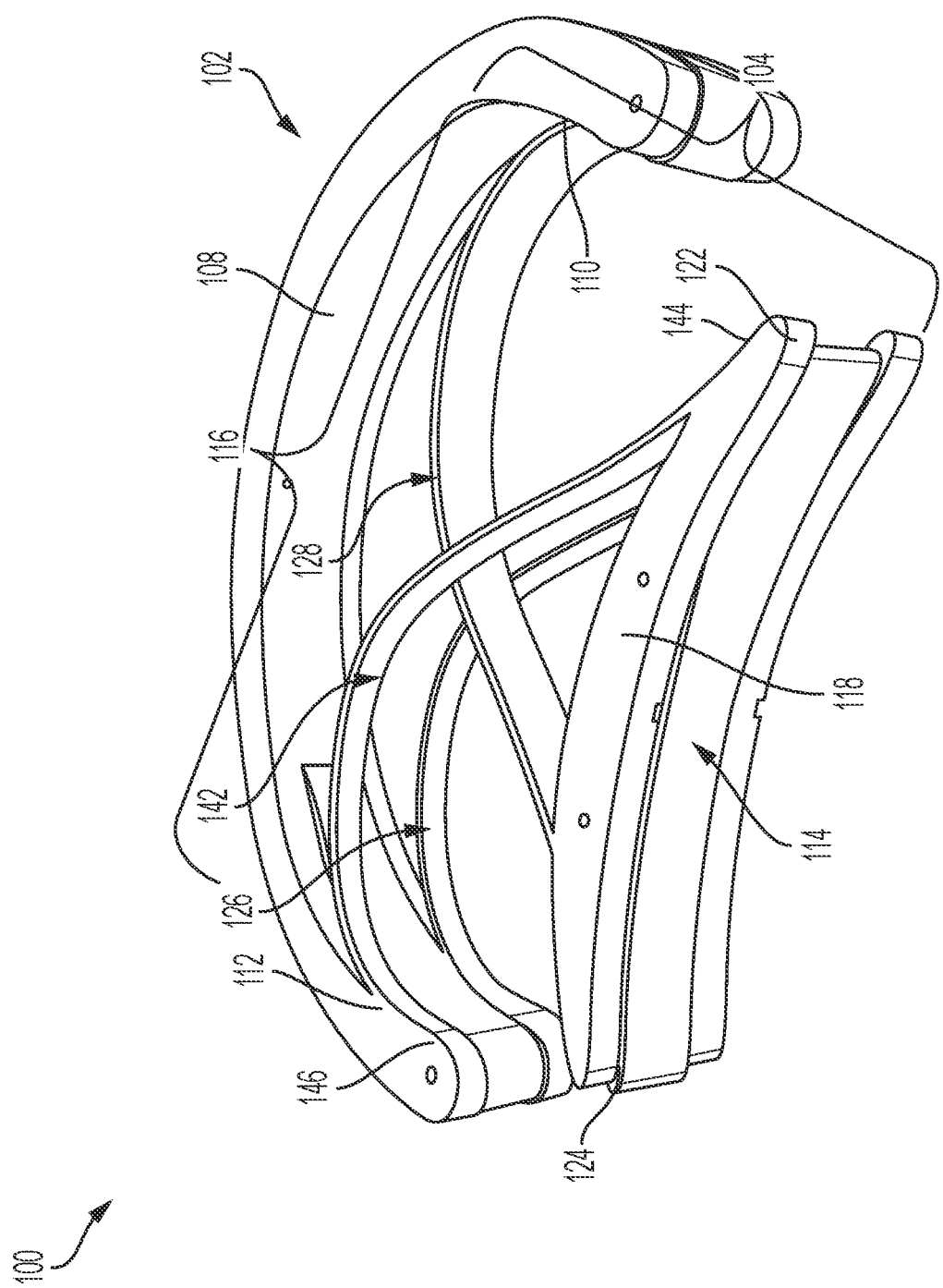
FIG. 4 depicts an example mechanism with three layers.
Figure 5:
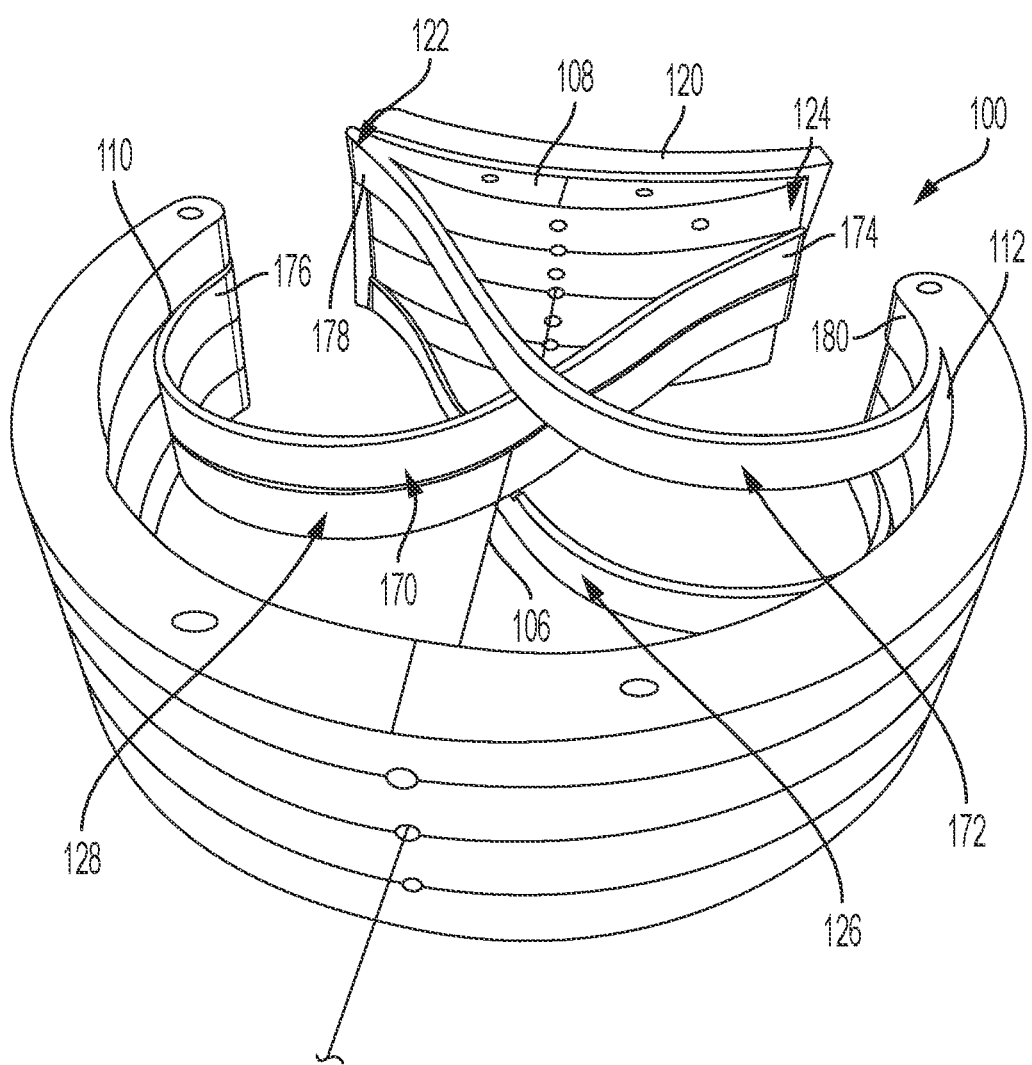
FIG. 5 depicts an example mechanism with four layers, with each layer being identical and stacked on top of each other in different configurations.

The wiper mechanism 104 primarily relies on two, three, or four compliant members which cross each other from opposite sides of the cylindrical shape. FIGS. 3-5 depict the two, three, and four compliant member versions. The compliant cross axis members store a certain amount of spring energy in their beams when the mechanism is in its undeployed state. When the user, such as a surgeon or surgical technician, is ready to wipe, actuator 106 tension is released (the tension holding the wiper in its undeployed state) and the compliant cross axis members' beam spring energy is released, deploying the wiper blade 114 and effectively wiping the lens 202.

FIG. 3 depicts an example of a base wiper mechanism 104 with two initially curved beams that are derived from elongated cross axis flexural pivots. Like the example of FIG. 1, the example cleaning device of FIG. 3 also makes use of a first curved cross member 126 and a second curved cross member 128. The first curved cross member 126 is on a first plane and has a first end 130 coupled to the first end 122 of the blade 114 and a second end 132 coupled to the second end 112 of the cavity 108. The second curved cross member 128 is on a second plane and a first end 134 coupled to the second end 124 of the blade 114 and a second end 136 coupled to the first end 110 of the cavity 108. The first curved cross member 126 and the second curved cross member 128 cross each other and bias the blade 114 in a first state where the blade 114 is in a deployed position but can deform allowing the blade 114 to transition to a second state in a stored position where the blade 114 is contained within the cavity 108 of the sheath 102. In this embodiment, the cleaning device 100 is formed on two layers with the first cross member 126 attached to the body 118 of the blade and a first layer 160 of the sheath 102 in a first plane. The second cross member 128 is attached to the body 118 of the blade 114 and a second layer 162 of the sheath 102 in a second plane. The second layer 162 is stacked on and attached to the first layer 160 of the sheath 102 forming the sheath 102. This separate layer formation and coupling allows the cross members 126, 128, body 118, and first 160 and second 162 layers to be formed as one piece. Here the one piece is formed of plastic. In other embodiments, the first curved cross member 126 and second curved cross member 128 can be co-planar wherein one curved cross member passes through the other curved cross member. The actuator 106, here a cable attached to the body 118 of the blade 114, can also be seen in this example. Other possible approaches and configurations will be apparent to one skilled in the art given the benefit of this disclosure.

FIG. 4 depicts an example wiper mechanism 104 with three layers. Here, in addition to the first curved cross member 126 and second curved cross member 128, there is a third curved cross member 142 on third plane having a first end 144 coupled to the first end 122 of the blade 114 and a second end 146 coupled to the second end 112 of the cavity 108. The third curved cross member 142 crosses the second curved cross member 128 and the thickness of the first curved cross member 126 and third curved cross member 142 equals the thickness of the second curved cross member 128. In this embodiment the wiper mechanism 104 is formed of three layers with final assembly of both the body 118 of the blade 114 and the sheath 102 being formed of the three layers with each layer formed as one piece. The combined widths of layer 1 and 3 equal layer 2. This ensures that during deployment and cocking, the blade 114 stays level relative to the face of the lens 202. Other possible approaches and configurations will be apparent to one skilled in the art given the benefit of this disclosure.

FIG. 5 depicts an example mechanism with four layers to limit the out of plane bending when moving across the lens 202. Here, in addition to the first curved cross member 126 and second curved cross member 128, there are two additional cross members, 170, 172 in a mirrored configuration. The third curved cross member 170 is on a third plane and has a first end 174 coupled to the second end 124 of the blade 114 and a second end 176 coupled to the first end 110 of the cavity 108. The fourth curved cross member 172 is on a fourth plane and has a first end 178 coupled to the first end 122 of the blade 114 and a second end 180 coupled to the second end 112 of the cavity 108. Here the first curved cross member 126 and the fourth curved cross member 172 cross the second cross member 128 and the third cross member 170. The thickness of the first curved cross member 126 and fourth curved cross member 172 equals the thickness of the second curved cross member 128 and the third cross member 170. In this embodiment the wiper mechanism 104 is formed of four layers with final assembly of both the body 118 of the blade 114 and the sheath 102 being formed of the four layers with each layer formed as one piece. A small gap exists between the second and third layers to allow the actuator 106, here a cable, to travel freely between.

While the examples FIGS. 3-5 show the sheath 102 made up of layers it should be understood that the sheath 102 can be formed of one solid piece. It should also be understood that the sheath 102 shown in these examples is truncated to focus on the wiper mechanism 104 and can be part of a larger sheath 102 that can extend along or otherwise encompasses an optical instrument 200. In some embodiments, the blade 114 or sheath 102, or portions thereof, can be formed of a translucent material to allow light from the optical instrument 200 to pass through the transparent portion. Other possible approaches and configurations will be apparent to one skilled in the art given the benefit of this disclosure.

Two primary characteristics apply to the wiper mechanism 104: compliant mechanism and developable mechanism principles.

The compliant cross axis members 126, 128, 142, 170, 172 are a unique design in that they are manufactured initially curved (to a great extent), compliant, and can cross each other on different planes without touching. These cross-axis members 126, 128, 142, 170, 172 store spring energy in their members, allowing the mechanism 116 to deploy and redeploy to its initially "cocked" state. The cross-axis members 126, 128, 142, 170, 172 also apply stability to the blade 114 itself to prevent it from rotating side-to-side or rotating in-plane. An example of the operation can be seen in FIG. 6A-C.

Figure 6A:
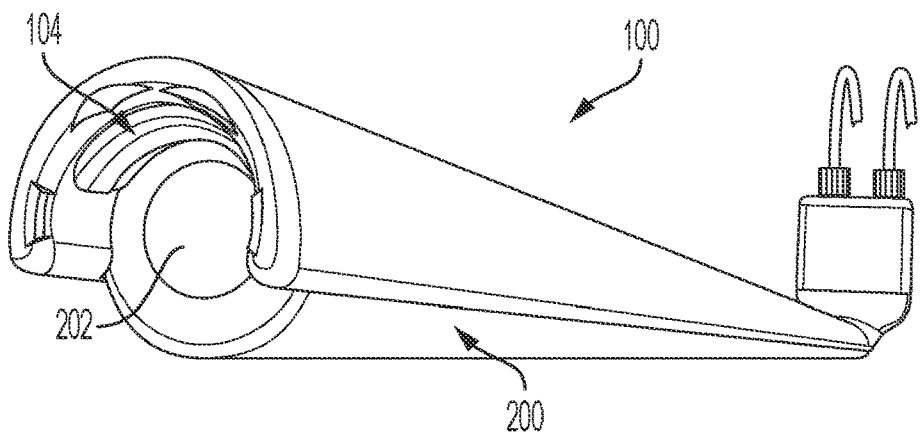
FIG. 6A-C depicts a deployment sequence of compliant members.
Figure 6B:
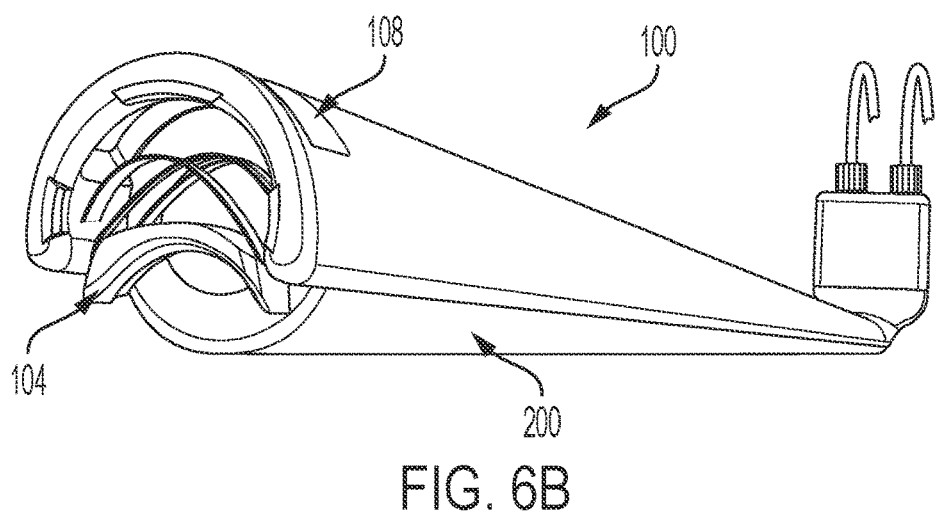
Figure 6C:
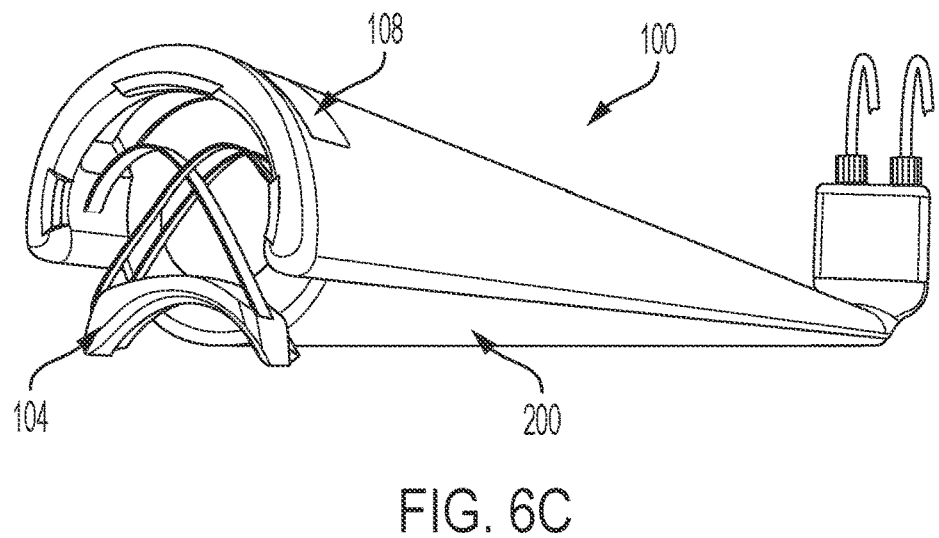

FIG. 6 shows the deployment of the wiper mechanism 104 of the cleaning device 100. In the image of FIG. 6A, the wiper mechanism 104 is in a second stored state where curved cross members 126, 128, 142 have been deformed such that the wiper mechanism is "stowed" with the compliant deployment mechanism 116 in a "cocked" state by an actuator 106 maintaining tension on the wiper mechanism 104 with stored spring force energy. In the image in the FIG. 6B, the tension on the wiper mechanism 104 has been released by the actuator 106, wherein the spring energy stored by the deformation of the curved cross members 126, 128, 142 of the compliant deployment mechanism 116 transitions the blade 114 to the first state in which it is biased by the curved cross members 126, 128, 142. The image of the FIG. 6C shows the wiper mechanism 104 fully deployed in the first state. To store the wiper mechanism 104 back to the second state, tension is reapplied by the actuator 106 wherein the wiper mechanism 104 transitions from the first state shown in the bottom image to stored second state shown in the top figure.

Blade

The blade 114 (also referred to as a wiper) itself is made of a few parts: The body 118 and the lens engagement surface 120. The body 118 holds the lens engagement surface 120 in place and as such is typically formed of a material that can provide suitable rigidity while still allowing for some flexibility. Examples of such materials include plastic and metal. In certain embodiments, the body may be formed of the same material as the curved cross members 126, 128, 142, 170, 172, and sheath 102. The lens engagement surface 120 is the part that makes physical contact with the lens 202 of the optical instrument 200. As such, the lens engagement surface 120 is typically made of a biocompatible rubber, silicone, or other comparable material. The lens engagement surface 120 can be adhered to the body 118, mechanically affixed to the body 118, or a combination thereof. In certain examples, the blade 114 is configured to clean or wipe in both directions with the cavity 108 being an opening in the rear, so debris does not get stuck behind the blade 114. In some embodiments, the body 118 or lens engagement portion 120, or portions thereof, can be formed of a translucent material to allow light from the optical instrument 200 to pass through the transparent portion. Other possible approaches and configurations will be apparent to one skilled in the art given the benefit of this disclosure.

Controls

Figure 7:
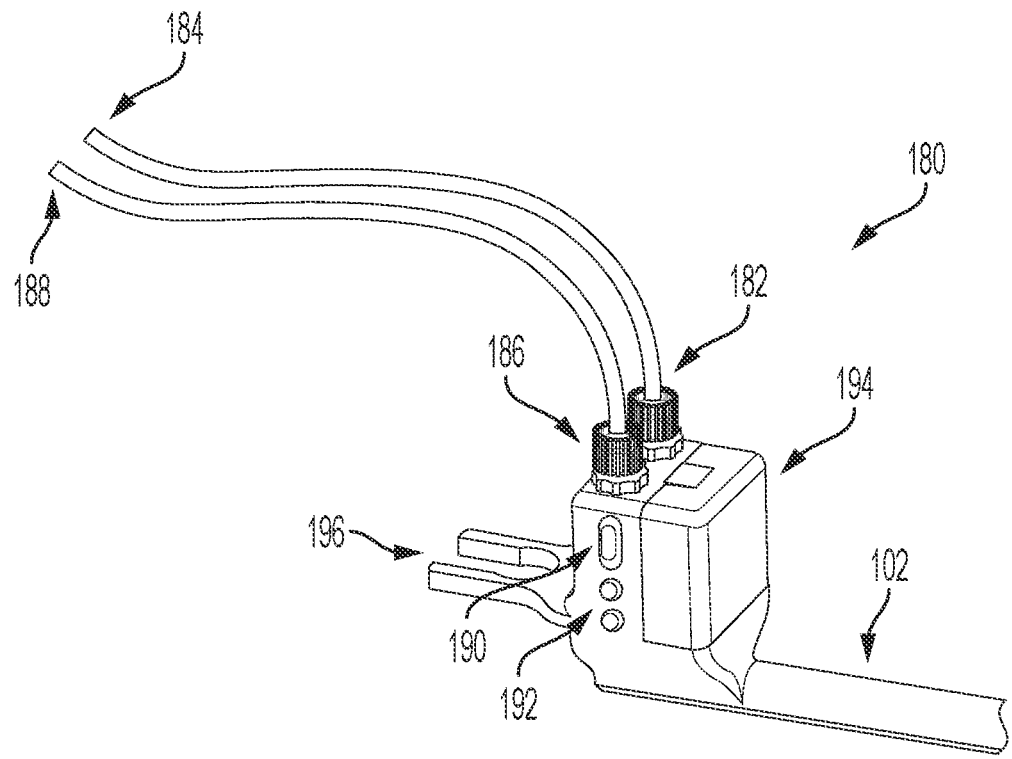
FIG. 7 depicts the proximal end of a laparoscope with electronic controls and fluid and gas hookups.
Figure 8:
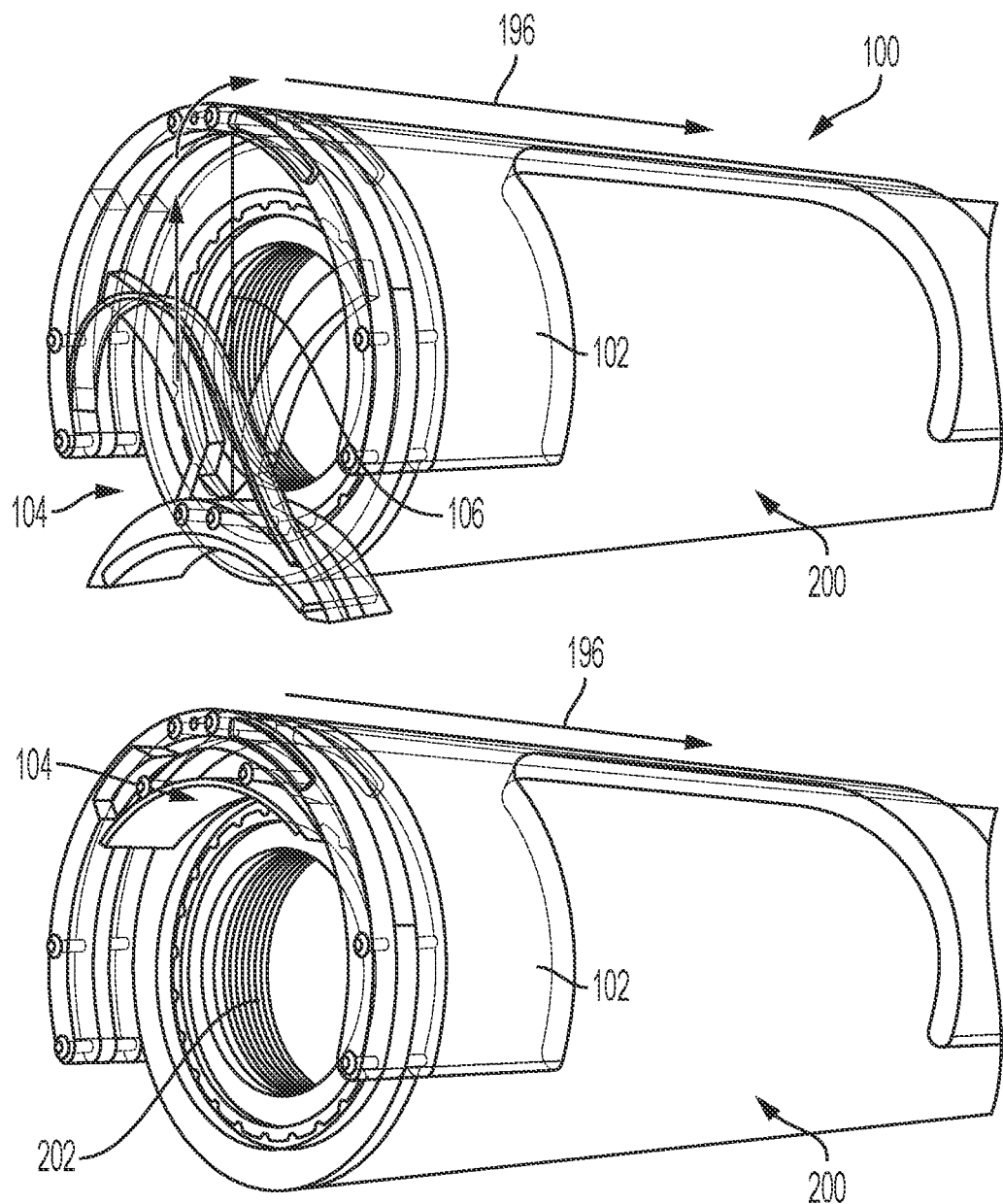
FIG. 8 depicts the operation of actuation cables.

In certain embodiments, the device 100 may be provided with a tensioning device, fluid and/or gas hook-ups, and controls for such operating such functionality which are located remotely from the wiper mechanism such that they are accessible ex vivo (outside the body) while the wiper mechanism 104 (and the lens 202 it cleans) are in-vivo (inside the body) at a distal end. FIG. 7 depicts an example proximal end 180 of the integrated cleaning device 100 showing the controls, battery pack, and luer lock attachments located at the other end of the sheath 102 from the wiper mechanism 104.

In the Example of FIG. 7 the proximal end 180 end includes luer lock attachment 182 which is in fluid communication with the port 138 on the distal end of the cleaning device 100 for connecting a gas source 184 providing gas to port 138, a luer lock attachment 186 which is in fluid communication with the one or more sprayers 140 on the distal end of the cleaning device 100 for connecting a fluid source 188 providing fluid to be dispensed by the sprayers 140, controls 190 for activating the wiper mechanism 104, controls 192 for activating the port 138 or sprayers 140, a battery pack 194 for powering one or more of the wiper mechanism 104, gas port 138, or sprayers 140, and a means 196 for attaching an optical instrument 200, such as laparoscope, to the cleaning device 100. Other possible approaches and configurations will be apparent to one skilled in the art given the benefit of this disclosure.

Actuation Method

Figure 9:
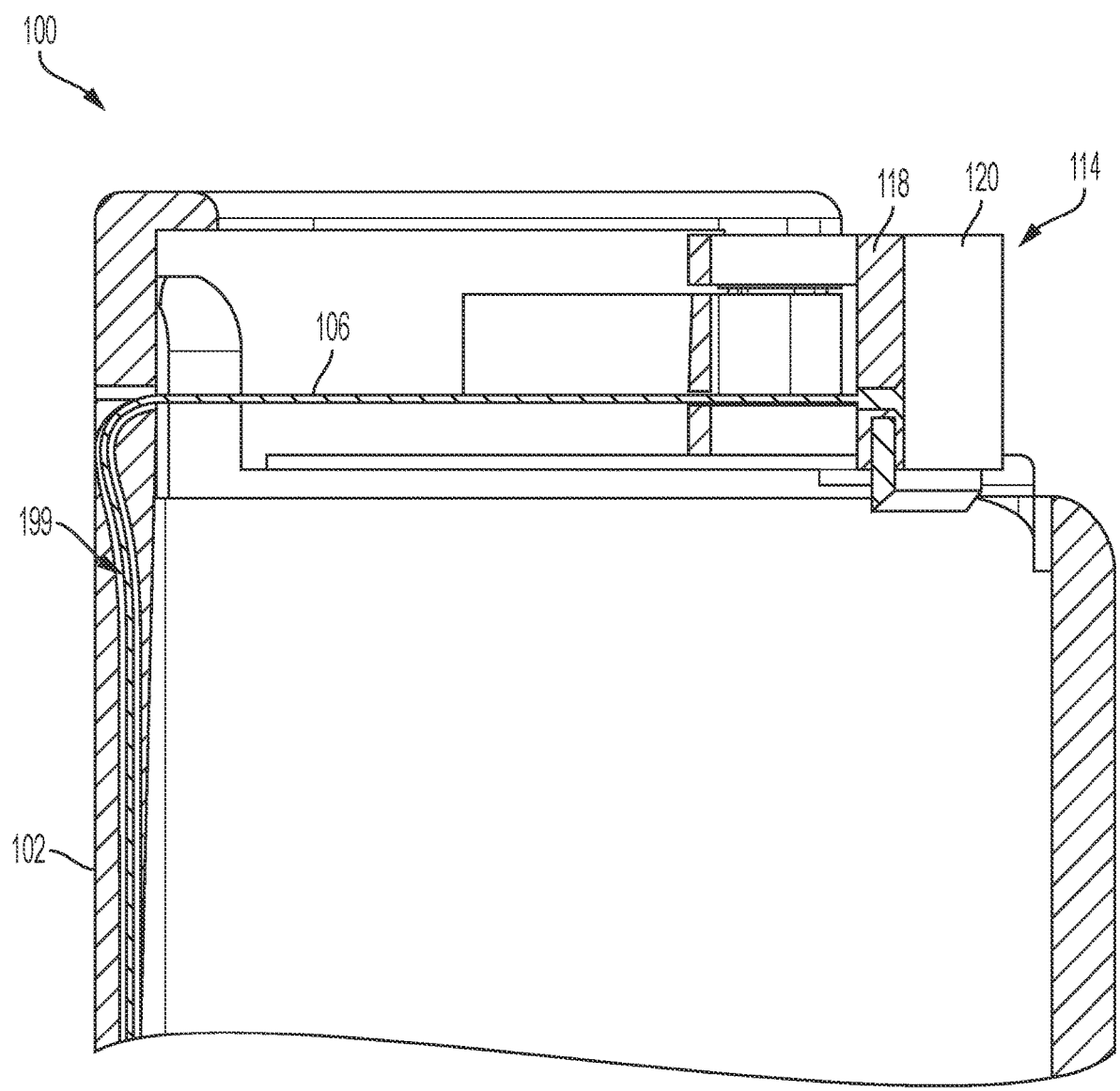
FIG. 9 depicts a channel for the actuation cable.

In certain embodiments, the actuator 106 is a cable. A biocompatible cable is connected to the body 118 of the blade 114 and then is put into tension (indicted by arrows 198) to bring the wiper mechanism 104 into its undeployed state, where it conforms to the cylinder shape of the optical instrument 200, such as a laparoscope. The tension is then released when the mechanism is ready to wipe. An example of the cable actuation can be seen in FIG. 8. The actuator 106 cable can be enclosed channel 199 in the sheath 102 as seen in FIG. 9 that runs along the optical instrument 200 and is then attached to either a mechanical trigger or an electric motor (e.g. servomotor) located distally from the wiper mechanism 104 at a proximal end 180 of the cleaning device 100 that tensions and de-tensions the actuator 106. In the example of FIG. 9. The actuator cable 106 is attached to the body 118 of the blade 114 at a point offset vertically from the center of the body 118. Offsetting the connection induces a downward force that helps keep the lens engagement portion 120 of the blade 114 in contact with the lens 202. An example of manual trigger 212 is a finger trigger that actuates the wiper mechanism 104, which can be seen in FIG. 10.

Figure 10:
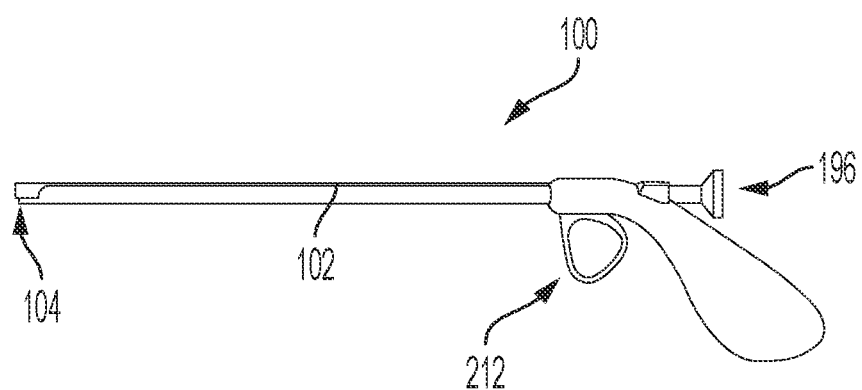
FIG. 10 depicts an example manual actuation method.
Figure 11:
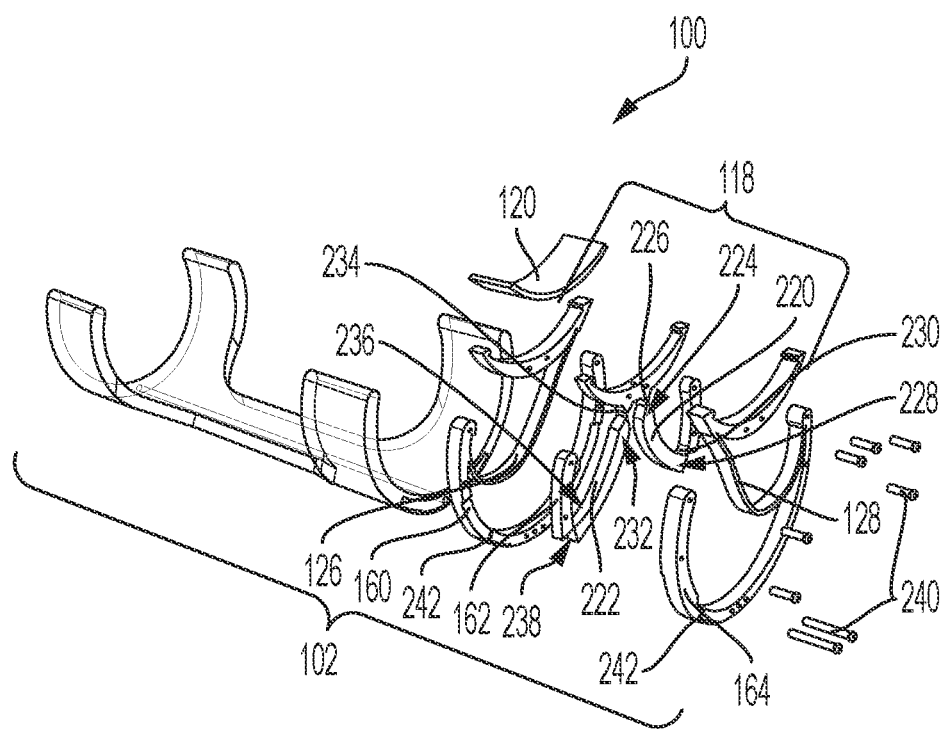
FIG. 11 depicts and exploded view of an example mechanism having complaint linkages and rigid members
Figure 12:
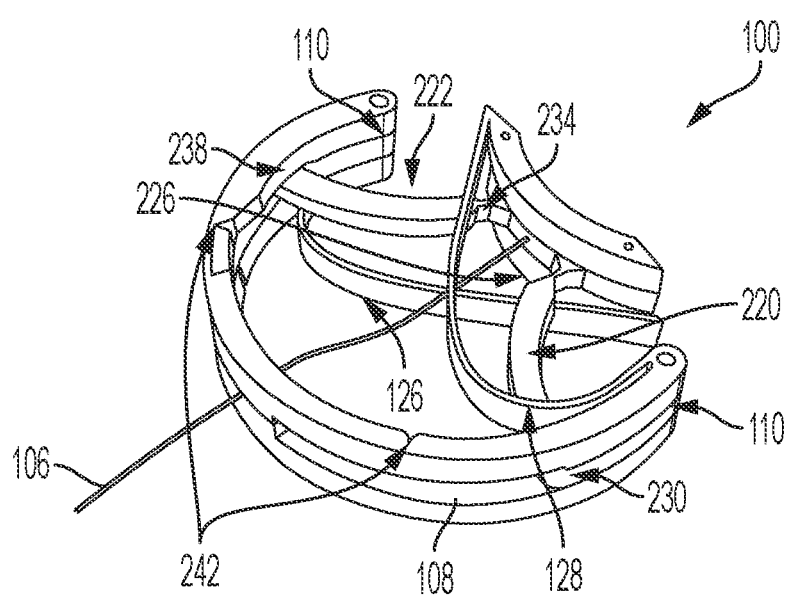
FIG. 12 depicts the assembled compliant linkages and rigid members used to implement the wiper mechanism.

In the embodiment of FIG. 10, the cleaning device 100 is show with a finger trigger 212 located at a remote distance from the wiper mechanism 104 of the cleaning device 100 below the attachment means. Here the attachment means 196 is an aperture into which an optical instrument 200 can be inserted such that the lens 205 of the optical instrument 200 is put in proximity to the wiper mechanism 104. Other possible approaches and configurations will be apparent to one skilled in the art given the benefit of this disclosure.

Stabilizing Component

To prevent out-of-plane bending motion, a separate layer or component can be attached to prevent unwanted bending. This ensures that the wiper can move across the face of the lens evenly. Examples of this can be seen in FIG. 11 and FIG. 12.

In this example, in in addition to the first curved cross member 126 provided on first layer 160 forming part of the sheath 102 and blade body 118 and second curved cross member 128 provided on a third layer 164 forming part of the sheath 102 and blade body 118, there are two additional rigid or non-compliant members 220, 222 provided on a second layer 162 between the first 160 and third layers 164. The second layer comprises a non-compliant or rigid curved third member 220 and a non-compliant or rigid fourth member 222.

The non-compliant or rigid third member 220 has a first end 224 coupled to a midpoint of the body 118 of the blade 114 at a first joint 226 and a second end 228 coupled to a second joint 230 offset from the first end 110 of the cavity 108 of the sheath 102. The non-compliant/rigid curved fourth member 222 has a first end 232 coupled to a midpoint of the body 118 of the blade 114 at a third joint 234 and a second end 236 coupled to a fourth joint 238 offset from the second end 112 of the cavity 108 of the sheath 102.

The layers 160, 162, 164 can be assembled together and attached to the rest of sheath 102 using screws 240 or other suitable fastening means. In certain embodiments, the non-compliant or rigid curved third member 220 and the non-compliant or rigid curved fourth member 222 are formed of plastic or other suitable material. In some such embodiments first 226, second 230, third 234, and fourth joint 238 comprise a living hinge. In certain embodiments the sheath portion 102 of the first layer 160 and third layer 164 are provided with flexural pivots 242 allowing the other circumference to expand to allow for the moving of the third 220 and fourth 222 rigid or non-complaint members when the wiper mechanism 104 transitions from the first open state to the second stored state.

The rigid or non-compliant third 220 and fourth 222 members provide additional rigidity preventing twisting or deformation of the blade 114 during use. In this embodiment, as the whole second layer 162 forming part of the sheath 102 and body 118 of the blade 114 is also formed of the rigid or non-compliant material the third 220 and fourth 222 members are formed of, the body 118 of the blade 114 is also reinforced.

Figure 13:
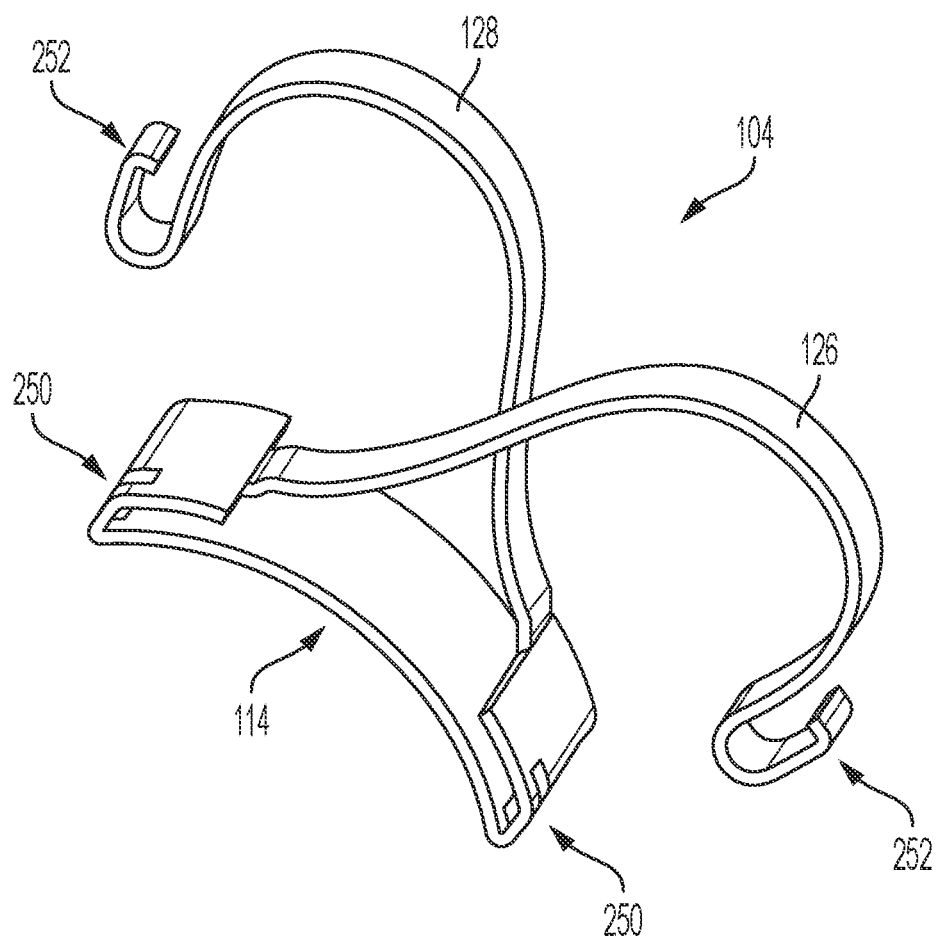
FIG. 13 depicts another embodiment of a wiper mechanism with slider groves cut out of the wiper mechanism and mechanism snap connection points.
Figure 14:
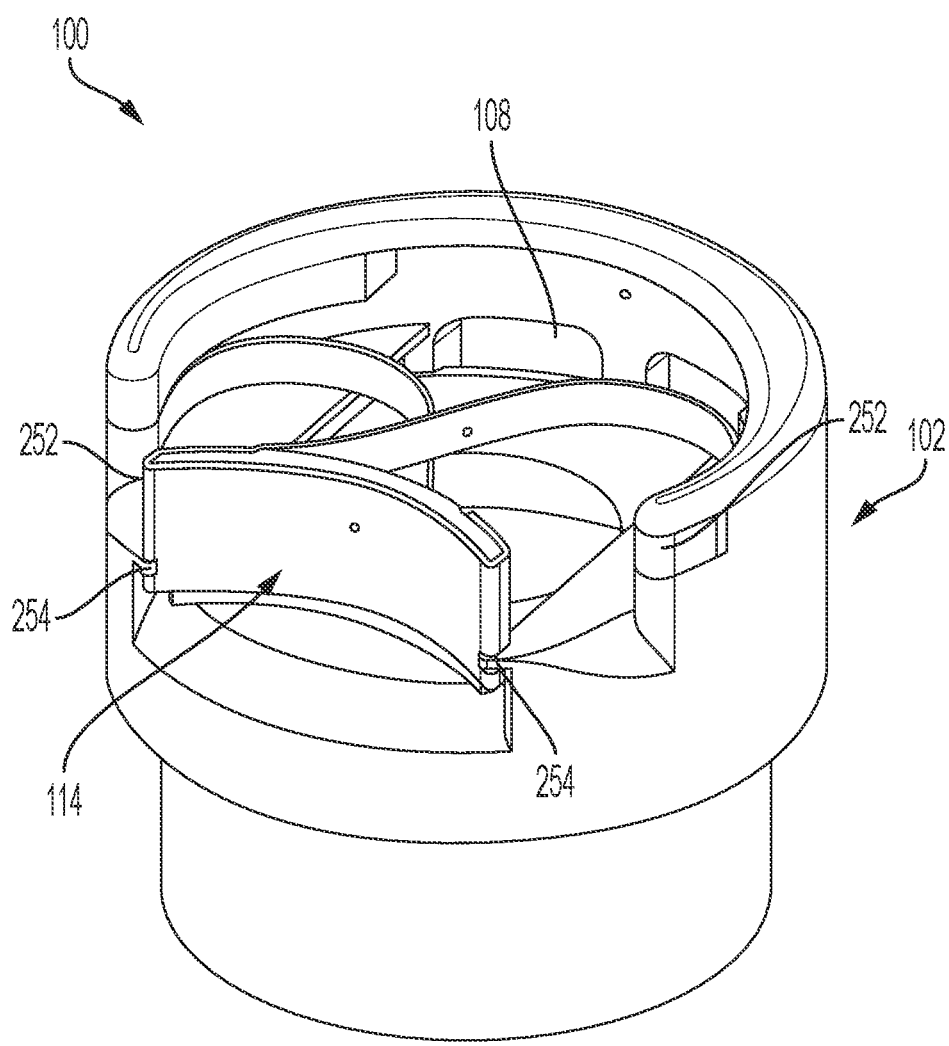
FIG. 14 depicts an embodiment of a sheath showing slider groves and the track of the wiper mechanism.
Figure 15:
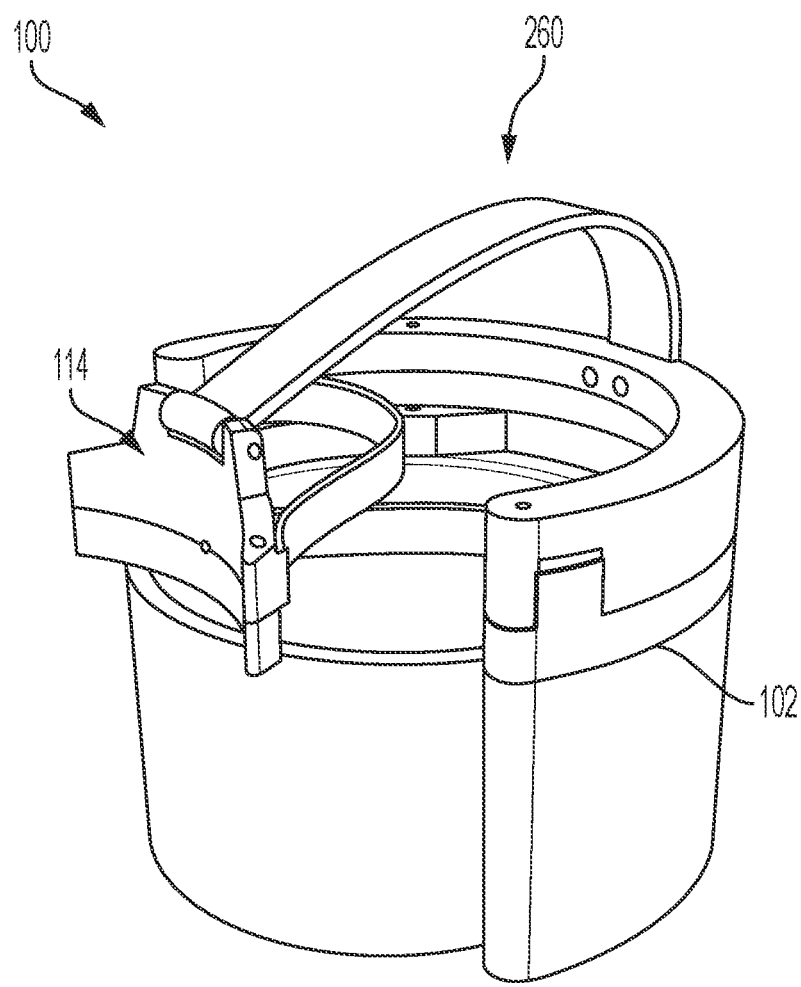
FIG. 15 depicts an embodiment with a compliant beam to apply a downward pressure on the wiping component.

In certain embodiments, in order to better control the pitch and pressure of the wiper mechanism 104 as it moves across the surface of the lens 202, a slider groove 250 and track 254 exist to control the pitch angle and consistent downward pressure, as shown in FIG. 13 and FIG. 14. FIG. 13 depicts an embodiment of a wiper mechanism 104 with slider grooves 250 cut out of the wiper blade 114 and mechanism snap connection points 252 on the compliant cross members 126, 128. FIG. 14 depicts the wiper mechanism 104 installed in a sheath 102 showing slider track 254 and snap connection points 252 of the device 100. The slider groove 250 and track 254 also constrains the blade 114 to always be a certain distance above the lens 202, thus allowing a consistent downward pressure during the entire deployment.

Another alternative stabilizing configuration is a compliant beam 260 that extends out of plane and applies a constant downward force during the wiping sequence. An example of this can be seen in FIG. 15. Here the compliant beam 260 is intended to apply a constant downward force for a more effective lens cleaning.

Sheath or Sleeve

The sheath 102 or sleeve is sized, shaped, and configured to attach to an optical instrument 200, such as a laparoscope, and respective equipment. The wiper mechanism 104 resides inside the cavity 108 of the sheath 102 which aligns with the distal lens of a laparoscope or endoscope. The sheath 102 or sleeve functions to secure the cleaning device 100 to the laparoscope and has a channel to allow the cable of the actuator 106 to travel through which is used for actuation. The sheath 102 or sleeve attaches to the proximal end of the laparoscope with an attachment means 196, such as clip or band.

Figure 16:
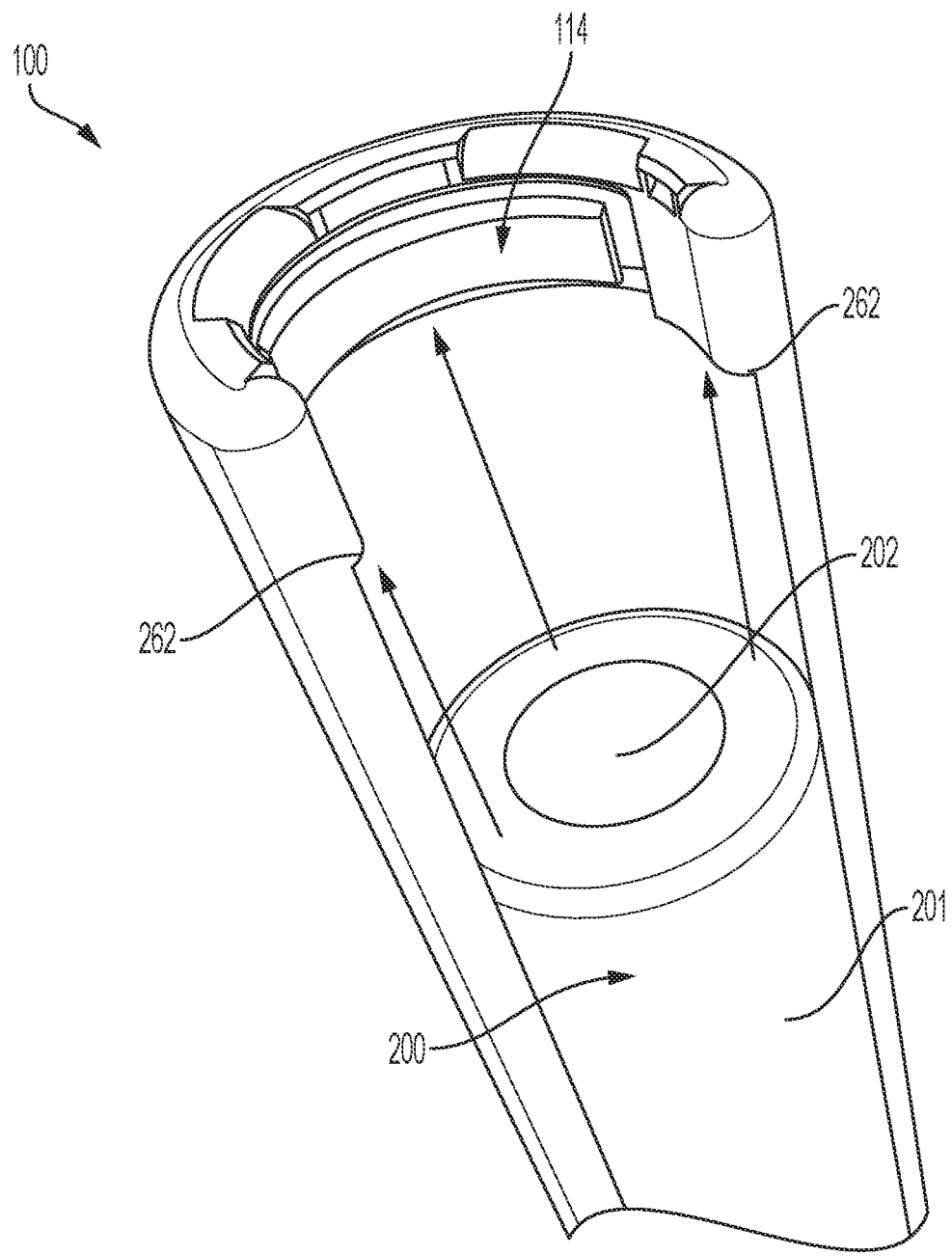
FIG. 16 depicts an example c-shaped sheath with hard stops.
Figure 17:
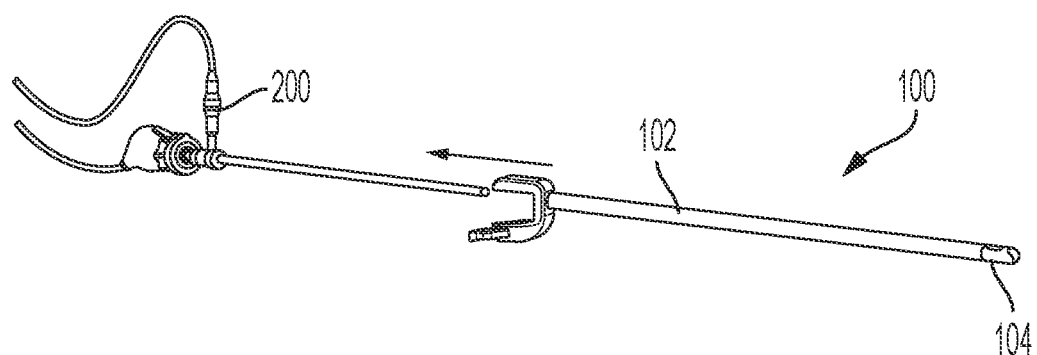
FIG. 17 depicts an example a laparoscope being inserted into a full cylindrical sheath.

In many of the previous embodiments and the example embodiment sheath 102 of FIG. 16, a C-shaped sheath 102 snaps onto the side of the laparoscope shaft 201 and is secured in place. The C-shape is a partial circle with an angle slightly greater that 180°, which allows it to snap around the laparoscope shaft 201 and be secured. The sheath is the slid down until it hits mechanical hard stops 262 to align the wiper blade 114 with the face of the lens 202.

As an alternative to the C-shaped sheath 102 that snaps on, a complete cylindrical sheath 102 that slides over the optical instrument 200 can be provided. An example of this can be seen in FIG. 17. The sheath 102 can either be a hard or soft plastic. In some embodiments, the sheath 102, or portions thereof, can be formed of a translucent material to allow light from the optical instrument 200 to pass through the transparent portion.

All embodiments secure the sheath 102 to the end of an optical instrument 200 and create a channel through which the actuator 106 cable can travel.

Gas and Fluid Integration

The cleaning device 100 of the present invention can be a multi-functional hybrid solution with both preventive and removal solutions. The wiper mechanism 104 is ideal for removing bodily fluids (e.g. blood) and debris (e.g. tissue particles) off the face of the lens. In order to prevent the frequent occurrence of fogging, in certain embodiments, a continuous stream of temperature-controlled gas 270 (e.g.

CO2) can be positioned accordingly on the distal end of the optical instrument 200 to blow across the face of the lens 202 from a port 138 preventing condensation buildup. An example of this can be seen in FIG. 18. Other streams of gas, continuous, intermittent, or repetitive on a predetermined cycle, are also anticipated for use with the present invention.

Figure 18:
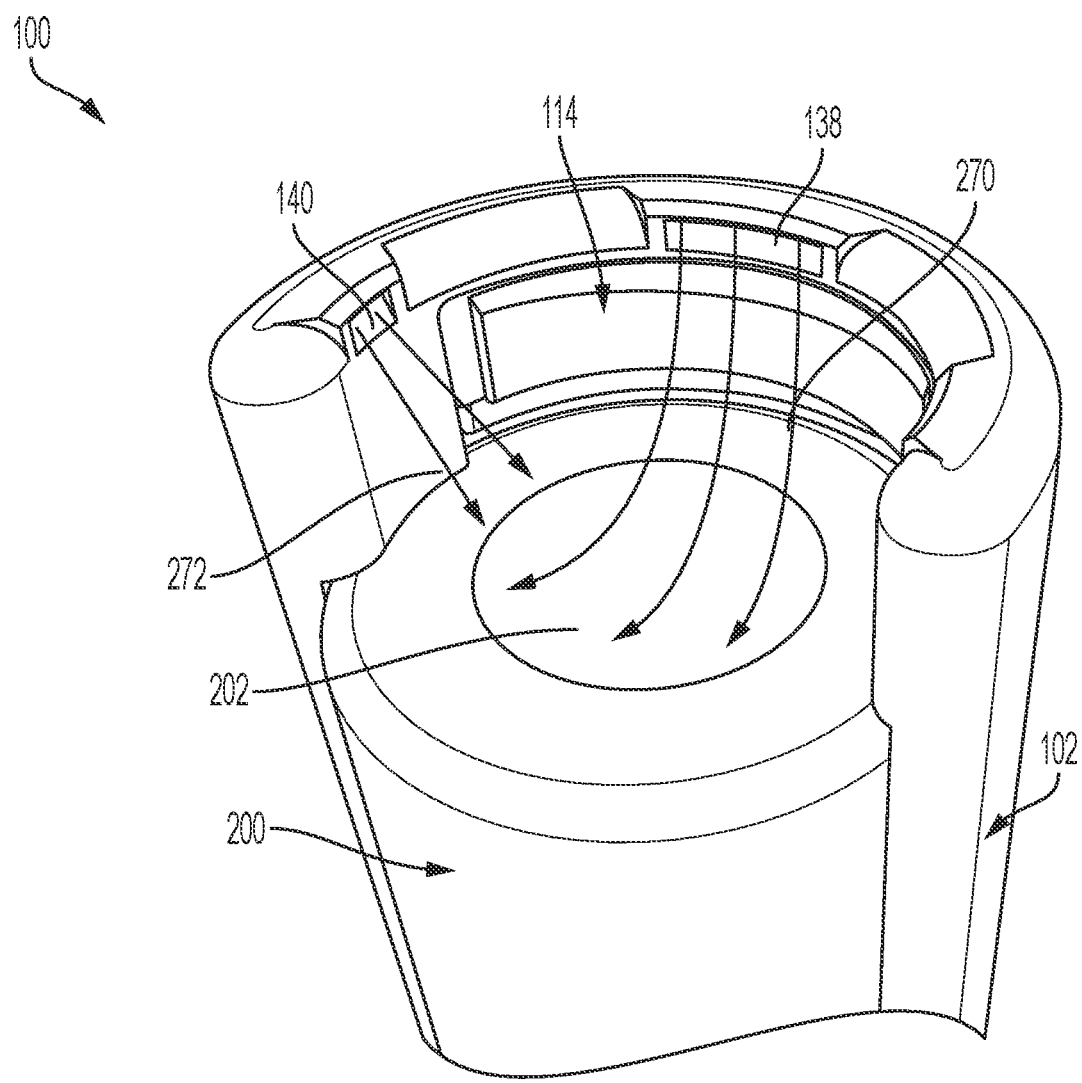
FIG. 18 depicts an example with gas integration and fluid sprayers.
Figure 19A:
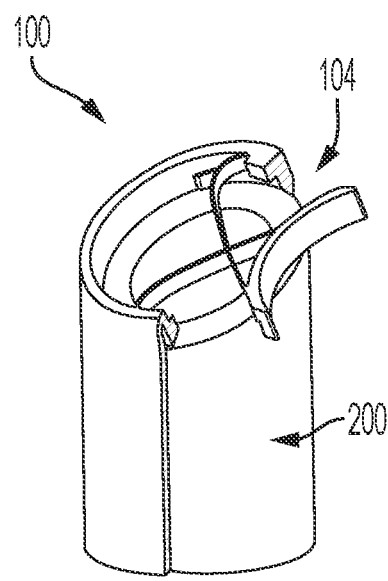
FIG. 19A-B depict various views of an example embodiment compatible with angled laparoscopes.
Figure 19B:
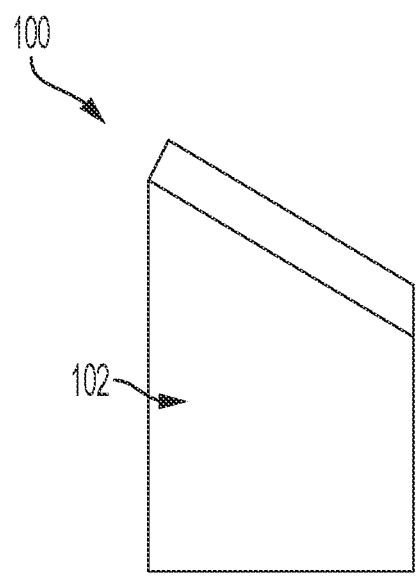
Figure 20A:
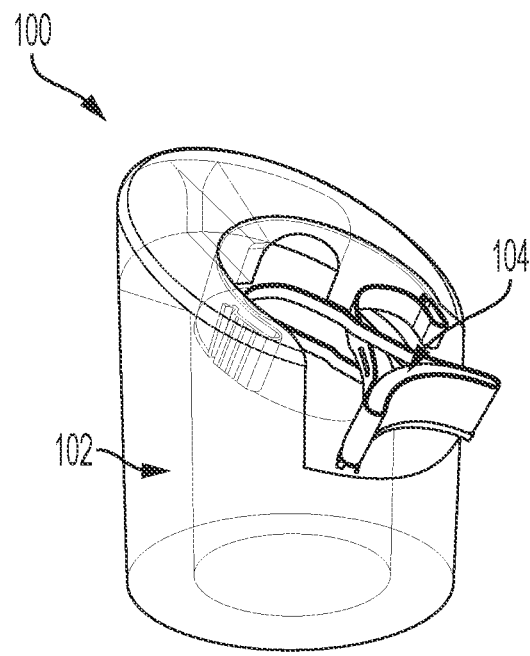
FIG. 20A-B depicts various views of another embodiment compatible with angled laparoscopes
Figure 20B:
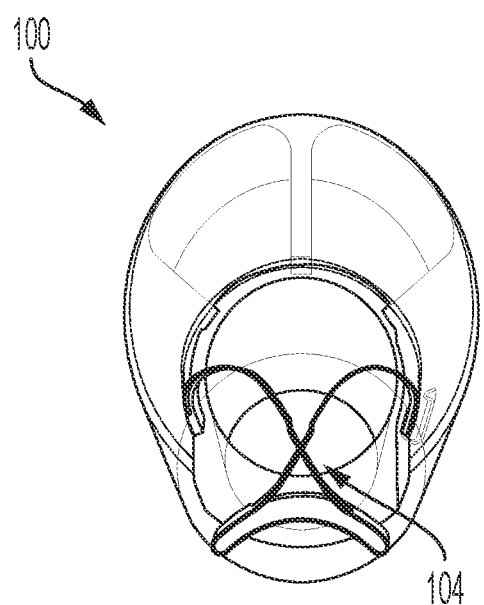
Figure 21:
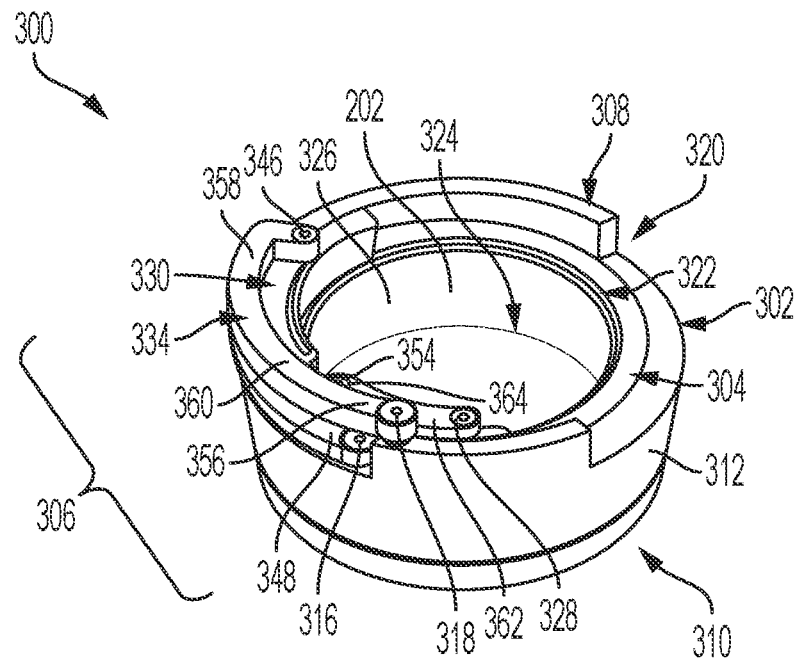
FIG. 21 depicts a rigid linked kinematic model of a wiper assembly.
Figure 21:
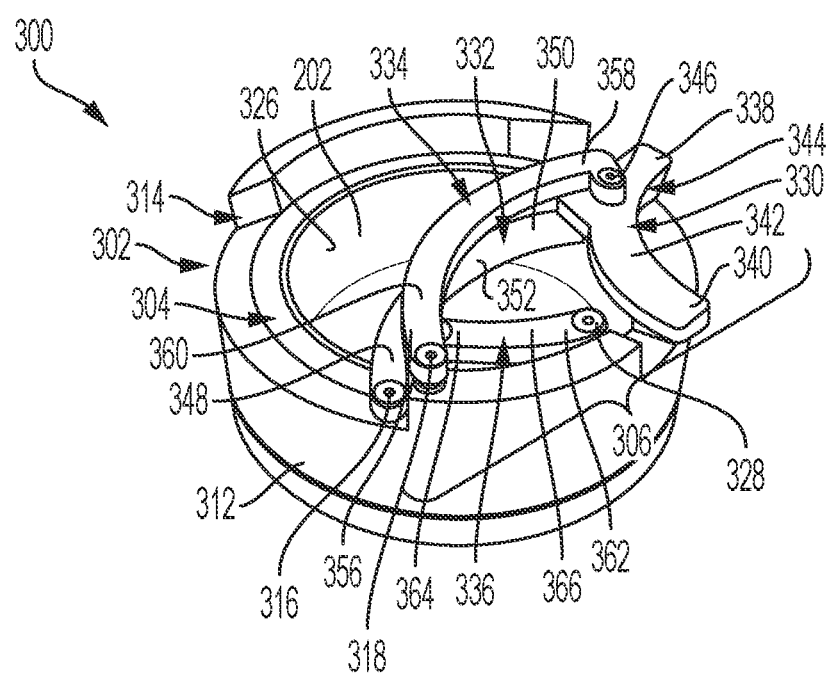

Additionally, one or more sprayers 140 can also be positioned and angled toward the face of the of the lens 202 and can be sprayed during a wiping sequence to facilitate the removal of debris. In the example of FIG. 18 there are sprayers 140 on the side for dispensing distilled water or saline 272.

Compatible with 0°, 30°, 70° Laparoscopes

While most of the previous example embodiments have the wiper mechanism 104 deploying perpendicular to the sheath 102 (so as to be parallel to the lens 205 of a 0-degree scope), the wiper mechanism 104 of the cleaning device 100 can be adapted to work at any number of angles offset from perpendicular (including 30-degrees and 70-degrees from perpendicular) thus making the cleaning device 100 compatible with 0, 30, and 70-degree scopes (or any other angle). An example of this can be seen in FIGS. 19A-19B and FIGS. 20A-20B. In certain embodiments the device is compatible with 5, 8, or 10 mm scopes. It should be understood that the mechanics allow for the design to be adapted for any angle or diameter.

Manufacturing and Assembly

Many of the previous example embodiments show how the components of the mechanism can be assembled together using multiple single layer components. It should be understood that components can be formed individually and assembled together or as a whole. In addition, components may be designed to snap together or otherwise attach without screws 240, or pins.

Non-Compliant Design

A rigid or non-compliant version of a cleaning device 300 can also be implemented. An example of this model can be seen in FIG. 21. Here the integrated cleaning device 300 for optical instruments comprises an outer cylinder 302 and an inner cylinder 304 that is rotated in relation to the outer cylinder 302 to actuate a developable wiper mechanism 306 between a stowed state as shown in the top image and a deployed state shown in the lower image.

The outer cylinder 302 comprises a first aperture at a first end 308, a second aperture at a second end 310, a first wall 312 extending between the first aperture and second aperture defining an outer circumference of the cleaning device 300, and a central passage therethrough from the first aperture to the second aperture. A first cavity 314 is disposed in the first wall 312 proximal to the lens 202 of the optical instrument 200 the first cavity 314 having a first joint 316 mounted in a first plane or elevation therein. A second joint 318 is mounted in a second plane or elevation therein adjacent along the circumference to the first joint 316. A second cavity 320 is disposed in the first wall 312 opposite the first cavity 314 proximal to the lens 202 of an optical instrument 200.

The inner cylinder 304 is disposed within the central passage of the outer cylinder 302 and comprises a first aperture at a first end 322 at the first plane of the first cavity 314 and second cavity 320, a second aperture at a second end 324, a second wall 326 extending between the first aperture and the second aperture defining an inner circumference of the cleaning device 300 and a central passage therethrough from the first aperture to the second aperture for receiving a lens 202 of an optical instrument 200. A third joint 328 is mounted in the first end 322 of the second wall 326.

The developable wiper mechanism 306 is disposed within the first cavity 314 and comprises a blade 330, a first support member 332, a second support member 334, and an actuation link 336.

The blade 330 comprises a first end 338 a second end 340 and a body 342 extending between the first end 338 and second end 340. The body 342 is curved to contour match the curvature of the second wall 326. A lens engagement surface 344 extends from the body 342 and configured to wipe the lens 202 of the optical instrument 200 upon movement of the body 342 across the lens 202. A fourth joint 346 is offset from the first end 338 of the blade 330.

The first support member 332 is in the first plane and comprises a first end 348 pivotably coupled to the first wall 312 of the outer cylinder 302 at the first joint 316; a second end 350 pivotably coupled to with the blade 330 at the fourth joint 346; a body 352 extending between first end 348 and second end 350, the body 352 curved to match the curvature of the first wall 312; and a fifth joint 354 offset from the first joint 316 on the body 352 of the first support member 332.

The second support member 334 is in the second plane and comprises a first end 356 pivotably coupled to the first wall 312 of the outer cylinder 302 at the second joint 318, a second end 358 pivotably coupled to the blade 330 at the fourth joint 346, and a body 360 extending between the first end 356 and second end 358. The body 360 is curved to match the curvature of the first wall 312.

The actuation link 336 is in the first plane and comprises a first end 362 pivotably coupled to the inner cylinder 304 at the third joint 328, a second end 364 pivotably coupled to the first support member 332 at the fifth joint 354, and a body 366 extending between the first end 362 and second end 364, the body 366 curved to match the curvature of the second wall 326.

When the inner cylinder 304 is rotated in relation to the outer cylinder 302 in such a way that moves the third joint 328 away from the first 316 and second 318 joint along the perimeter of the cleaning device 300, the developable wiper mechanism 306 transitions from a first state wherein the body 352 of the first support member 332 and the body 360 of the second support member 334 are within the first cavity 314 and the body 342 of the blade 330 and the body 366 of the actuation link 336 align with the inner perimeter of the second wall 326, to a second state where the first 332 and second 334 support member swing into the central passage moving the blade 330 across the central passage to wipe the lens 202 of the optical instrument 200.

The rigid or non-compliant version of the device 300 has all rigid components connected by pin joints and has some but not all of the advantages of the compliant version discussed herein.

Manufacturing Methods

By using precision stamping or precision flat spring manufacturing methods, the wiper mechanism 104 can be manufactured from a single piece of metal 400 that is bent/formed into place. Some examples of this can be seen in FIG. 22 where the piece of metal 400 is folded, as shown in successive images, resulting in the wiper mechanism 104. The wiper mechanism 104 can then snap onto the rest of sheath 102 as set forth above. The benefits of this manufacturing method will allow it to be more feasible to manufacture compared to precision injection molding or other alternatives previously mentioned. The design can either be 2-layer or a sandwiched 3-layer for symmetric bending.

As another alternative to precision stamping or flat spring manufacturing, a similar approach is wire forming, which can have one continuous wire that is bent and formed into a certain configuration for the wiper mechanism.

Figure 22:
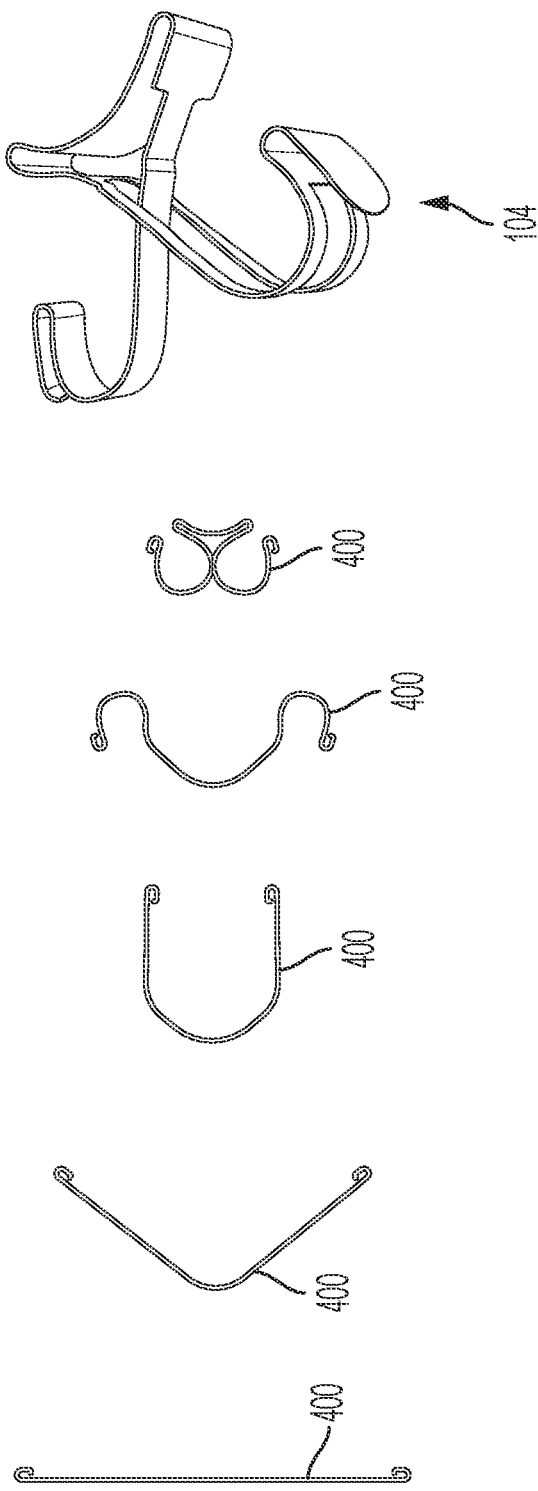
FIG. 22 depicts example wiper mechanism manufactured from a single piece of metal that is bent/formed into place.
Figure 23A:
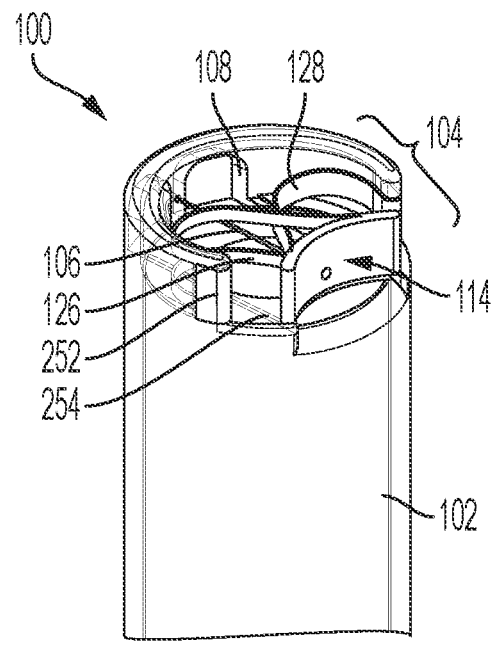
FIG. 23A is a front perspective view of another cleaning mechanism.
Figure 23B:
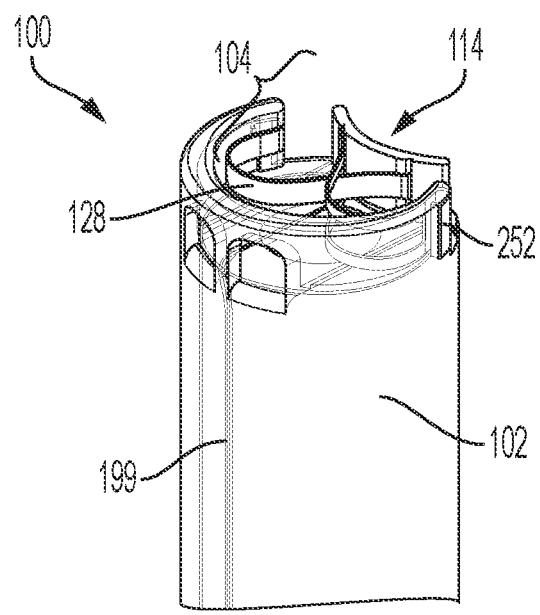
FIG. 23B a rear perspective view of the cleaning mechanism of FIG. 23A

FIGS. 23A-23B depict an assembled wiper mechanism formed as shown in FIG. 22 attached to the rest of the cleaning device 100. In these examples, the wiper mechanism 104 can be attached to the sheath 102 without adhesives or fasteners using friction and the snap connection points 252. In this embodiment, the first curved compliant member 126 is split allowing the second curved compliant member 128 to pass through it. This embodiment further makes use of slider track 254 to control the pitch angle and consistent downward pressure.

Figure 24:
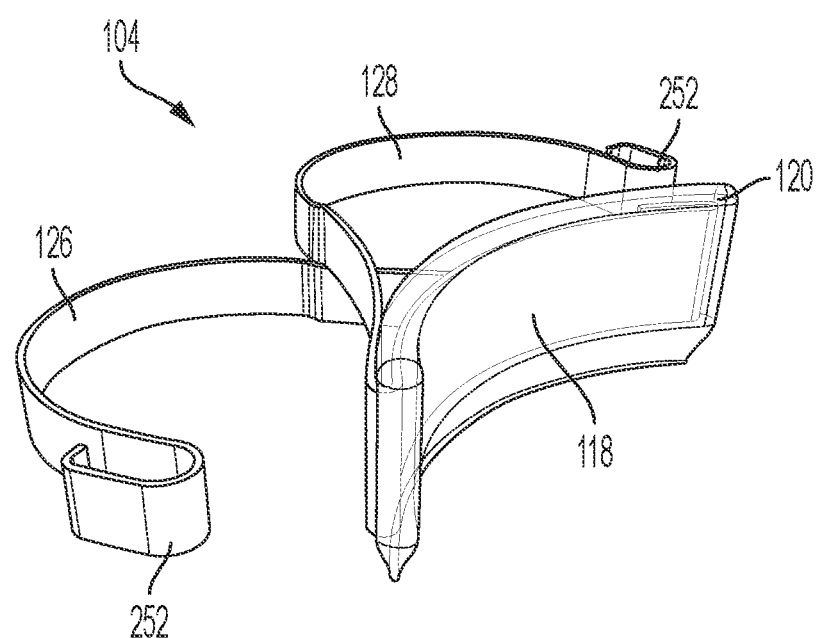
FIG. 24 depicts another wiper mechanism attached to a sheath.
Figure 25A:
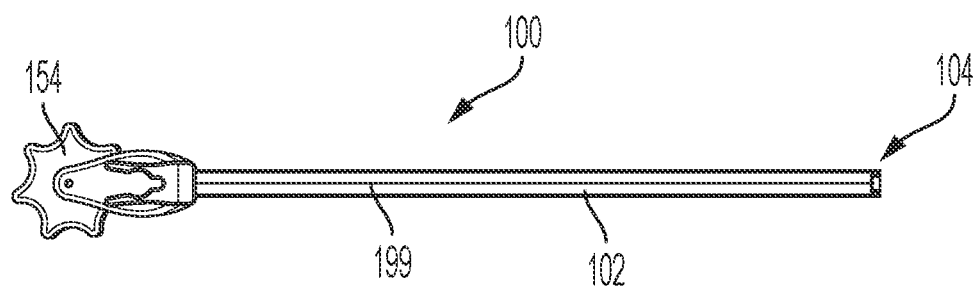
FIG. 25A depict a top view of an example laparoscope having turn disc activation.
Figure 25B:
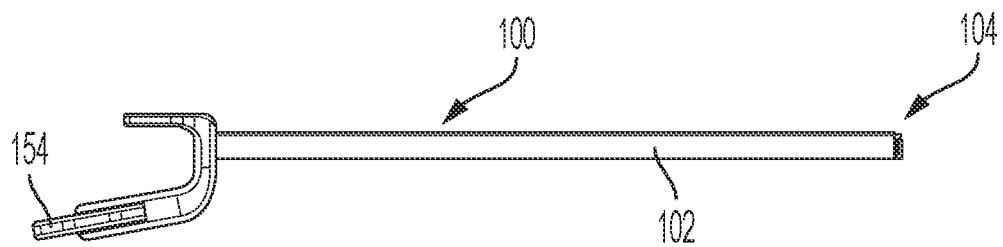
FIG. 25B depict a top view of an example laparoscope having turn disc activation.
Figure 26:
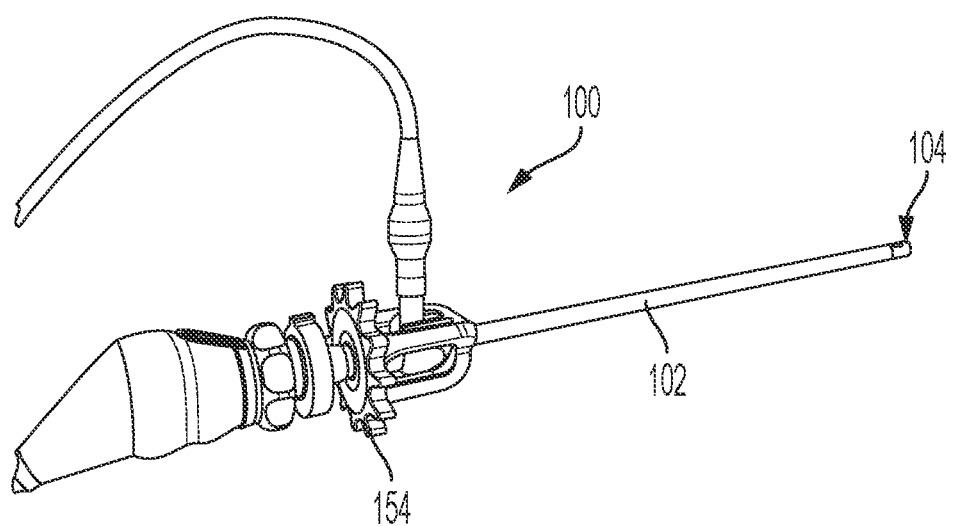
FIG. 26 depicts another example laparoscope having turn disc activation.

FIG. 24 depicts an over-molded lens engagement surface 120 sized and configured to fit over the body 118 of the blade 114. As the lens engagement surface is formed of deformable rubber or silicone, this can "fit over" the body 118 substantially encapsulating the edges of the body so as not requiring adhesives or fasteners to attach to the body 118 of the blade 114.

Disc or Wheel Actuation

In certain embodiments of the present invention, actuation of the device can involve a wheel actuator 154 that is connected to a cam system connected to the actuator that will deploy the wiper mechanism 104 with each click. An example of this can be seen in FIGS. 25A and 25B.

In still other embodiments, the wheel actuator 154 can also be aligned in parallel to the focus wheel of the laparoscope, with the cams orthogonal to the wheel actuator 154. An example of this can be seen in FIG. 26.

Method of Use

Figure 27:
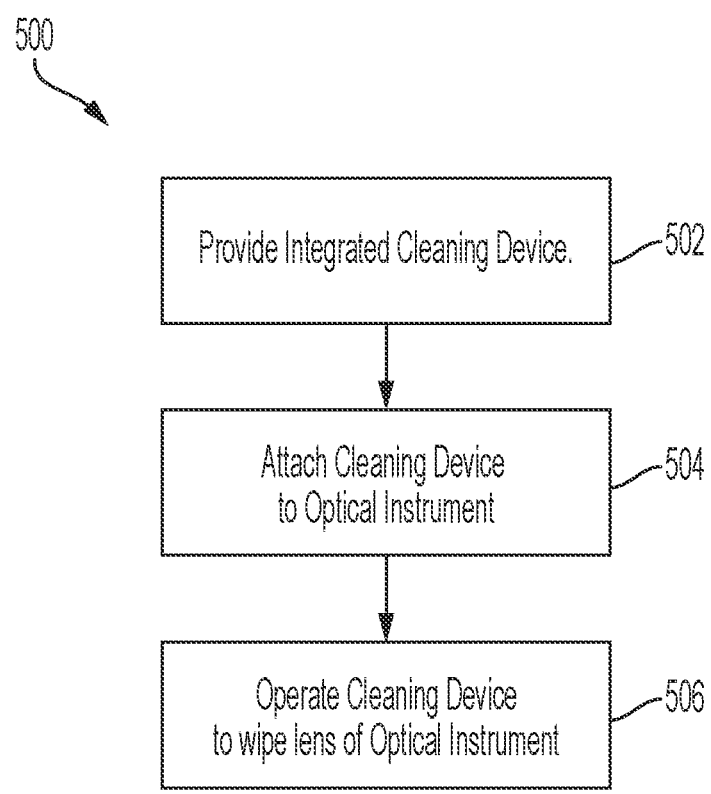
FIG. 27 is a flow diagram for cleaning an optical instrument using the integrated cleaning device of the present invention.

FIG. 27 depicts a flow chart depicting an example methodology 500 for cleaning an optical instrument. The first step of the method is to provide an integrated cleaning device 100, 300 as set forth and described herein (Step 502). The cleaning device can use a compliant deployment mechanism 116 such as the cleaning device 100 discussed herein or a non-compliant deployment mechanism 306 such as cleaning device 300 discussed in relation to FIG. 21. The next step is attaching the cleaning device 100, 300 to an optical instrument 200, such as a laparoscope (Step 504). The cleaning device 100, 300 can be attached as discussed in relation to FIG. 16 and FIG. 17. The final step is operating the cleaning device 100, 300 to wipe the lens of the optical instrument (Step 506). In the case of the compliant wiper mechanism 116 cleaning device 100, this involves releasing tension maintained by the actuator 106 using tensioner mechanism such as a trigger 152, knob or wheel 154, or electronic controls 190 wherein the wiper mechanism 104 transitions from a second state to a first state as described in relation to FIG. 6. In the case where the cleaning device 300 uses a non-complaint mechanism 306, this involves rotating the inner cylinder 304 in relation to the outer cylinder as set forth in regard to FIG. 21.

To any extent utilized herein, the terms "comprises" and "comprising" are intended to be construed as being inclusive, not exclusive. As utilized herein, the terms "exemplary", "example", and "illustrative", are intended to mean "serving as an example, instance, or illustration" and should not be construed as indicating, or not indicating, a preferred or advantageous configuration relative to other configurations. As utilized herein, the terms "about" and "approximately" are intended to cover variations that may existing in the upper and lower limits of the ranges of subjective or objective values, such as variations in properties, parameters, sizes, and dimensions. In one non-limiting example, the terms "about" and "approximately" mean at, or plus 10 percent or less, or minus 10 percent or less. In one non-limiting example, the terms "about" and "approximately" mean sufficiently close to be deemed by one of skill in the art in the relevant field to be included. As utilized herein, the term "substantially" refers to the complete or nearly complete extend or degree of an action, characteristic, property, state, structure, item, or result, as would be appreciated by one of skill in the art. For example, an object that is "substantially" circular would mean that the object is either completely a circle to mathematically determinable limits, or nearly a circle as would be recognized or understood by one of skill in the art. The exact allowable degree of deviation from absolute completeness may in some instances depend on the specific context. However, in general, the nearness of completion will be so as to have the same overall result as if absolute and total completion were achieved or obtained. The use of "substantially" is equally applicable when utilized in a negative connotation to refer to the complete or near complete lack of an action, characteristic, property, state, structure, item, or result, as would be appreciated by one of skill in the art.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. Within this specification embodiments have been described in a way which enables a clear and concise specification to be written, but it is intended and will be appreciated that embodiments may be variously combined or separated without parting from the invention. It is intended that the present invention be limited only to the extent required by the appended claims and the applicable rules of law.

While many of the examples disclosed herein deal with laparoscopes, the teaching herein could be applied to any number of endoscopes. In addition, the teachings herein could be adapted to other optical instruments, such as dental mirrors to prevent fogging and wipe away spatter. It is also to be understood that the following claims are to cover all generic and specific features of the invention described herein, and all statements of the scope of the invention which, as a matter of language, might be said to fall therebetween.

The invention claimed is:

1. An integrated cleaning device for optical instruments, the device comprising:
   a sheath sized, shaped, and configured to attach to an optical instrument and having a cavity positioned in proximity to a lens of the optical instrument, the cavity having a first end and a second end;
   a wiper mechanism disposed within the cavity of the sheath, the wiper mechanism comprising:
   a blade comprising:
   a body having a first end and a second end opposite the first end, the body shaped in conformance with the size, shape, and configuration of the sheath; and
   a lens engagement surface extending from the body and configured to wipe the lens of the optical instrument with movement of the blade body; and
   a compliant deployment mechanism comprising:
   a first curved cross member having a first end coupled to the first end of the blade body and a second end coupled to the second end of the cavity; and a second curved cross member having a first end coupled to the second end of the blade body and a second end coupled to the first end of the cavity;

wherein the first curved cross member and the second curved cross member cross each other and bias the blade in a first state where the blade is in a deployed position but can deform allowing the blade to transition to a second state in a stored position where the blade is contained within the cavity of the sheath; and an actuator configured to transition the wiper mechanism between the first state to the second state wherein the actuator maintains tension on the blade to keep the blade in the second state and when the actuator releases tension on the blade, spring energy stored by the deformation of the first and second curved cross members is released transitioning the blade to the first deployed position providing a wipe of the wiper mechanism.

2. The device of claim 1, wherein the sheath is substantially cylindrical in shape or has a "C" shape cross-section.

3. The device of claim 1, wherein the optical instrument is an in-vivo medical instrument.

4. The device of claim 3, wherein the in-vivo medical instrument is an endoscope.

5. The device of claim 1, wherein the body of the blade and the first and second curved cross members are formed as one piece.

6. The device of claim 1, wherein the lens engagement surface is formed of rubber or silicone.

7. The device of claim 1, wherein the wiper mechanism further comprises:

a third curved cross member having a first end coupled to the first end of the blade body and a second end coupled to the second end of the cavity, wherein the third curved cross member crosses the second curved cross member and a thickness of the first curved cross member and third curved cross member equals a thickness of the second curved cross member.

8. The device of claim 7, wherein the body of the blade, the first curved cross member, the second curved cross member, and the third curved cross member are formed as one piece.

9. The device of claim 1, wherein the wiper mechanism further comprises:

a third curved cross member having a first end coupled to the second end of the blade body and a second end coupled to the first end of the cavity; and a fourth curved cross member having a first end coupled to the first end of the blade body and a second end coupled to the second end of the cavity;

wherein the first curved cross member and the fourth curved cross member cross the second cross member and the third cross member; and wherein a thickness of the first curved cross member and fourth curved cross member equals a thickness of the second curved cross member and the third cross member.

10. The device of claim 1, wherein the wiper mechanism further comprises:

a non-compliant/rigid curved third member having a first end coupled to a midpoint of the body of the blade at a first joint and a second end coupled to a second joint offset from the first end of the cavity; and a non-compliant/rigid curved fourth member having a first end coupled to a midpoint of the body of the blade at a third joint and a second end coupled to a fourth joint offset from the second end of the cavity.

11. The device of claim 1, wherein the actuator comprises a cable attached to the body of the blade and extending through the sheath to a tensioner located distal from the wiper mechanism.

12. The device of claim 1, wherein the wiper mechanism further comprises a compliant beam between the blade and the sheath for maintaining a position of the blade in relation to the lens of the optical instrument.

13. The device of claim 1, further comprising at least one of a port in proximity to the lens of the optical instrument for providing a flow of gas across the lens or a spray in proximity to the lens of the optical instrument for applying a fluid to the lens.

14. The device of claim 13, further comprising controls for activation of at least one of the port or the sprayer.

15. The device of claim 1, wherein the wiper mechanism is deployed substantially perpendicular to the sheath.

16. The device of claim 1, wherein the wiper mechanism is deployed at approximately a 30-degree angle from perpendicular to the sheath or approximately a 70-degree angle from perpendicular to the sheath.

17. The device of claim 1, wherein the sheath further comprises a stop for positioning the sheath on the optical instrument so that the wiper mechanism is proximal to the lens of the optical instrument.

18. The device of claim 1, wherein a portion of the device is transparent allowing light from the optical instrument to pass through the transparent portion.

* * * * *